United States Patent
Kang et al.

(10) Patent No.: US 10,165,972 B2
(45) Date of Patent: *Jan. 1, 2019

(54) APPARATUS AND METHOD FOR DETECTING NIR FLUORESCENCE AT SENTINEL LYMPH NODE

(71) Applicant: INTHESMART CO. LTD., Seoul (KR)

(72) Inventors: Uk Kang, Seoul (KR); Ilhyung Shin, Jeju-si (KR)

(73) Assignee: INTHESMART CO., LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/708,158

(22) Filed: Sep. 19, 2017

(65) Prior Publication Data
US 2018/0000401 A1 Jan. 4, 2018

Related U.S. Application Data

(63) Continuation-in-part of application No. 14/327,797, filed on Jul. 10, 2014, now Pat. No. 9,795,338.

(30) Foreign Application Priority Data

Jul. 12, 2013 (KR) .................. 10-2013-0081980

(51) Int. Cl.
*A61B 6/00* (2006.01)
*A61B 5/00* (2006.01)
(Continued)

(52) U.S. Cl.
CPC .......... *A61B 5/418* (2013.01); *A61B 1/0005* (2013.01); *A61B 1/00009* (2013.01);
(Continued)

(58) Field of Classification Search
None
See application file for complete search history.

(56) References Cited

U.S. PATENT DOCUMENTS 6,059,720 A    5/2000  Furusawa et al.
6,293,911 B1 *  9/2001  Imaizumi ........... A61B 1/00009
                                                  600/160
(Continued)

FOREIGN PATENT DOCUMENTS

EP       0792618 A1    9/1997
JP    2006340796 A    12/2006

OTHER PUBLICATIONS

UK Combined Search and Examination Report for application No. GB1411868.1 dated Dec. 1, 2014.

*Primary Examiner* — Joel F Brutus
(74) *Attorney, Agent, or Firm* — Patent Office of Dr. Chung Park

(57) ABSTRACT

A device for observing a sentinel lymph node (SLN) in a human body. More particularly, the present invention relates to a device for observing an SLN by detecting near-infrared (NIR) fluorescence caused by a fluorescent material such as indocyanine green (ICG) at the SLN and a method for detecting NIR fluorescence at an SLN. Particularly, in the implementation of a composite image obtained by reproducing a fluorescent material such as ICG and NIR fluorescence emitted by excitation light together with a visible light image, it is possible to detect an SLN with high accuracy through a color contrast method and/or a temporal modulation method using an NIR fluorescence image signal and a visible reflection light image signal.

11 Claims, 24 Drawing Sheets
(7 of 24 Drawing Sheet(s) Filed in Color)

(51) Int. Cl.
*A61B 1/06* (2006.01)
*A61B 1/00* (2006.01)
*A61B 1/04* (2006.01)

(52) U.S. Cl.
CPC .............. *A61B 1/043* (2013.01); *A61B 1/063* (2013.01); *A61B 1/0638* (2013.01); *A61B 5/0071* (2013.01); *A61B 5/0086* (2013.01); *A61B 5/7425* (2013.01)

(56) References Cited

U.S. PATENT DOCUMENTS

| | | |
|---|---|---|
| 2002/0013531 A1 | 1/2002 | Hayashi |
| 2003/0078477 A1 | 4/2003 | Kang et al. |
| 2004/0010192 A1 | 1/2004 | Benaron et al. |
| 2004/0225222 A1 | 11/2004 | Zeng et al. |
| 2007/0203413 A1 | 8/2007 | Frangioni |
| 2007/0276257 A1* | 11/2007 | Heanue ................ A61B 5/0059 600/476 |
| 2011/0063427 A1 | 3/2011 | Fengler et al. |
| 2011/0104071 A1 | 5/2011 | Lee et al. |
| 2011/0249323 A1 | 10/2011 | Tesar et al. |

* cited by examiner

APPARATUS AND METHOD FOR DETECTING NIR FLUORESCENCE AT SENTINEL LYMPH NODE

CROSS-REFERENCE TO RELATED APPLICATION

This application is a continuation-in-part of U.S. patent application Ser. No. 14/327,797 filed Jul. 10, 2014, which claims under 35 U.S.C. § 119(a) the priority benefit of Korean Patent Application No. 10-2013-0081980 filed Jul. 12, 2013, the disclosures of all applications of which are incorporated herein by reference.

BACKGROUND

(a) Technical Field

The present invention relates to a device for observing a sentinel lymph node (SLN) in a human body. More particularly, the present invention relates to a device for observing an SLN by detecting near-infrared (NIR) fluorescence caused by a fluorescent material such as indocyanine green (ICG) at the SLN and a method for detecting NIR fluorescence at an SLN.

(b) Background Art

Sentinel lymph node (SLN) is a lymph node that cancer cells firstly reach when the tumor is directly metastasized via lymph nodes. SLN biopsy is a method for identifying metastasis by finding an SLN through injection of a color pigment into cancer tissue, excising the SLN and then performing a histopathologic examination on the excised SLN. If a cancer is detected in the SLN, all lymph nodes around the cancer are excised. However, if the cancer is not detected in the SLN, it is determined that the cancer is not metastasized to the SLN, and the excision of the SLN can be minimized.

As such, the SLN biopsy can minimize, through minimum excision of lymph nodes, side effects and complications, which may be generated by completely excising peripheral lymph nodes together with cancer tissues in the existing operations. The SLN biopsy has been already performed as a standard surgical technique in breast cancer, melanoma, etc. In addition, the SLN biopsy is being extended to surgical operations in the fields of all cancers including lung cancer, esophageal cancer, stomach cancer, thyroid cancer, gynecological cancer, urologic cancer, laryngeal cancer, etc.

In the SLN biopsy, the position of the SLN cannot be exactly detected with the naked eye. Hence, a nuclear medicine imaging method using a radioactive isotope as a tracer, an imaging method using a magnetic fluid having magnetism, an optical imaging method using a vital dye, or a method simultaneously using a radioactive isotope and a vital dye is used in the SLN biopsy.

An optical imaging method and various fluorescent materials as vital dyes have been studied to minimize radiation exposure to a patient and to detect the SLN. For example, studies on an optical imaging probe for SLN detection including a poly-gamma-glutamic acid and an optical imaging dye complex have been conducted. Among fluorescent dyes, the use of indocyanine green (ICG) is permitted in many countries including FDA in USA. The ICG allows light to be excited in a near-infrared (NIR) region, and generates fluorescent light. In addition, the internal structure of human tissue distributed up to a depth of 10 to 20 mm can be observed using the ICG, and NIR fluorescent light can be observed even at a place where white visible light is thrown, such as an operating room.

However, such an NIR fluorescent dye cannot be seen with the naked eyes, and thus devices capable of observing NIR fluorescent light have been developed. As a result, a device called hyper eye medical system (HEMS) was recently developed for observing NIR during surgery.

The HEMS device is an imaging device for observing ICG fluorescent light. The HEMS device simultaneously measures visible light and NIR using a single camera 3 installed therein, and NIR fluorescent light can be observed even in an environment with bright external illumination. The HEMS device is shown in FIG. 1.

The HEMS device employs, together with a white light source 1, a light source (NIR LED) having a wavelength of 760 nm as an excitation light source 2. However, through the device having the structure described above, the external appearance of an opened organ can be seen only during an abdominal surgery, and there often occurs a confusion among the color of visible light, an ICG fluorescent image in an NIR combined image and an image caused by glare of white light reflected on the surface of a human body.

Meanwhile, Japanese Patent Application Publication No. 2006-340796 has disclosed a system for detecting an SLN from a fluorescent image. Particularly, in Japanese Patent Application Publication No. 2006-340796, white light including excitation light is emitted by a xenon lamp, and an excitation light filter is set to allow light of a wavelength band of 385 to 435 nm to be transmitted therethrough. In the case of fluorescent light and background light, obtained from an object to be measured, a light-shielding filter is inserted between an object to be observed and a single CCD chip to allow the fluorescent light and the background light to be transmitted therethrough. Thus, an image is picked up in the CCD chip. In addition, the image is processed by a TV camera to be shown as a fluorescent image through a monitor. However, the system is a device for a contrast medium which emits fluorescent light in visible light such as 5-ALA. The device is not suitable for observing fluorescent light in NIR, such as ICG.

In relation to this, U.S. Patent Application Publication No. 2011/0063427 discloses an imaging system for providing full-color reflection light and NIR image. The imaging system for obtaining the NIR and full-color image includes a light source which supplies visible light and NIR light to an object to be observed, and a camera having a plurality of image sensors which independently detect blue reflection light and green reflection light from the object to be observed, and alternately detect red reflection light and NIR light generated from the object to be observed.

A controller for transmitting a signal to the light source and the camera controls consecutive blue and green lights to be irradiated onto the object to be observed, and red light and NIR excitation light are synchronized by periodically switching on-off the light source and the camera so that red and NIR fluorescent images are alternately obtained from the camera.

A red reflection light spectrum and an NIR light spectrum are alternately obtained from the same image sensor through the switching synchronization between the light source and the camera. Thus, the red reflection light spectrum provides, together with the blue and green reflection lights, a full-color image, or the NIR light spectrum provides an NIR fluorescent image. However, the synchronization between the light source and the camera makes the device complicated.

Meanwhile, in an imaging system for simultaneously observing a wide range of spectra from visible light (400 to 700 nm) to NIR light (700 to 900 nm), a chromatic aberration correction is required to adjust the focus on the focal plane of an image obtaining chip such as a CCD sensor. U.S. Patent Application Publication No. US2011/0249323 A1 discloses a special optical coupler for correcting a chromatic aberration in an endoscope device. The disclosed optical coupler is configured with an afocal prism assembly and an imaging optics. The afocal prism assembly is configured with prisms having different refractive indices, and dichroic coating is performed at the boundary between the prisms, so that an incident wavelength is incident onto an appropriate prism. The chromatic aberration between visible light and NIR light, which pass through prisms having different refractive indices, is corrected by correcting the difference in light path length between the visible light and the NIR light. However, a specific optical system is required to remove the chromatic aberration in such a manner, and the existing optical couplers cannot be used.

In addition, when a visible light image and an NIR image are respectively displayed in two different screen windows of the same monitor or when the two images are displayed to overlap with each other, it is difficult to distinguish the visible light image from the NIR image.

Basically, the distinguishment of the SLN from a non-SLN depends on the intensity of a fluorescent signal. Even when the same device is used, the intensity of the fluorescent signal is considerably changed depending on a distance to an object to be observed, parameters (gain, shutter and frame) set in the detection sensitivity of a TV system, the intensity of excitation light, etc. Therefore, a standard measuring method is essentially required to ensure the reliability of a detection result.

SUMMARY OF THE DISCLOSURE

The present invention provides a device and a method for detecting near-infrared (NIR) fluorescence at a sentinel lymph node (SLN), which can detect NIR fluorescence and an SLN with high accuracy in the implementation of a composite image obtained by reproducing NIR fluorescence emitted by excitation light from a fluorescent material such as indocyanine green (ICG) together with a visible light image.

In accordance with one aspect of the present invention, a device for detecting near-infrared (NIR) fluorescence at a sentinel lymph node (SLN), the device comprises a white light source configured to irradiate white light onto an object, a near-infrared (NIR) excitation light source configured to irradiate near-infrared (NIR) excitation light onto the object, an optical analyzing assembly configured to transmit white reflection light reflected off the object when the white light is irradiated on the object and near-infrared (NIR) fluorescence reflected off the object when the near-infrared (NIR) excitation light is irradiated on the object, a multispectral image processing unit configured to detect the white reflection light and the near-infrared (NIR) fluorescence, transmitted from the optical analyzing assembly, and process the white reflection light and the near-infrared (NIR) fluorescence as a visible (VIS) reflection light image signal and a near-infrared (NIR) fluorescence image signal, respectively; and a display unit configured to output a composite image obtained by combining the visible (VIS) reflection light image signal and the near-infrared (NIR) fluorescence image signal, processed by the multispectral image processing unit, wherein the multispectral image processing unit splits the visible (VIS) reflection light image signal into red (R), green (G) and blue (B) image signals, and performs image processing so that the visible (VIS) reflection light image signal is expressed by a first color composed of red (R), green (G) and blue (B) in a pixel from which an NIR where the near-infrared (NIR) fluorescence image signal is not detected, and the NIR near-infrared (NIR) fluorescent image signal is expressed by a second color, which is different from the first color, in a pixel where the near-infrared (NIR) fluorescent image signal is detected In an exemplary embodiment, the multispectral image processing unit extracts a color histogram for the visible reflection light image signal and sets a color having a little or no frequency in the color histogram to the second color.

In accordance with another aspect of the present invention, a device for detecting near-infrared (NIR) fluorescence at a sentinel lymph node (SLN), the device comprises a white light source configured to irradiate white light onto an object, a near-infrared (NIR) excitation light source configured to irradiate near-infrared (NIR) excitation light onto the object, an optical analyzing assembly configured to transmit white reflection light reflected off the object when the white light is irradiated on the object and near-infrared (NIR) fluorescence reflected off the object when the near-infrared (NIR) excitation light is irradiated on the object, a multispectral image processing unit configured to detect the white reflection light and the near-infrared (NIR) fluorescence, transmitted from the optical analyzing assembly, and process the white reflection light and the near-infrared (NIR) fluorescence as a visible (VIS) reflection light image signal and a near-infrared (NIR) fluorescence image signal, respectively; and a display unit configured to output a composite image obtained by combining the visible (VIS) reflection light image signal and the near-infrared (NIR) fluorescence image signal, processed by the multispectral image processing unit, wherein the multispectral image processing unit splits the visible (VIS) reflection light image signal into red (R), green (G) and blue (B) image signals, and performs image processing so that the visible (VIS) reflection light image signal is expressed by a first color composed of red (R), green (G) and blue (B) in a pixel from which an NIR where the near-infrared (NIR) fluorescence image signal is not detected, and the NIR near-infrared (NIR) fluorescent image signal is expressed by a second color, which is at least one of red (R), green (G) and blue (B), in a pixel where the near-infrared (NIR) fluorescent image signal is detected, wherein if the second color is same with the first color, the multispectral image processing unit controls a grayscale of at least one of the first color and the second color to be adjusted or controls a timing pulse of the near-infrared (NIR) fluorescent image signal so that the second color is discontinuously implemented.

In an exemplary embodiment, the multispectral image processing unit may extract a color histogram for the visible reflection light image signal and sets a color having a little or no frequency in the color histogram to the second color.

In another exemplary embodiment, the grayscale of the first color and the grayscale of the second color may be adjusted so that a difference between the grayscale of the first color and the grayscale of the second color is equal to or greater than a specific threshold value.

In still another exemplary embodiment, the grayscale of the first color and the grayscale of the second color may be relatively adjusted.

In still another exemplary embodiment, the timing pulse of the near-infrared fluorescence image signal may be adjusted periodically or non-periodically with a time interval.

In accordance with one aspect of the present invention, a method for detecting near-infrared (NIR) fluorescence at a sentinel lymph node (SLN), the method comprises irradiating white light and NIR near-infrared (NIR) excitation light onto an object; collecting white reflection light reflected off the object when the white light is irradiated onto the object and near-infrared (NIR) fluorescence reflected off the object when the near-infrared (NIR) excitation light is irradiated onto the object; performing image processing so that the white reflection light is expressed by a first color which is composed of red (R), green (G), blue (B) and the near-infrared (NIR) fluorescence is expressed by a second color which is different from the first color; and generating a composite image by combining the white reflection light having the first color and the near-infrared (NIR) fluorescence having the second color.

In accordance with another aspect of the present invention, a method for detecting near-infrared (NIR) fluorescence at a sentinel lymph node (SLN), the method comprises irradiating white light and NIR near-infrared (NIR) excitation light onto an object; collecting white reflection light reflected off the object when the white light is irradiated onto the object and near-infrared (NIR) fluorescence reflected off the object when the near-infrared (NIR) excitation light is irradiated onto the object; performing image processing so that the white reflection light is expressed by a first color which is composed of red (R), green (G), blue (B) and the near-infrared (NIR) fluorescence is expressed by a second color; and generating a composite image by combining the white reflection light having the first color and the near-infrared (NIR) fluorescence having the second color, wherein if the second color is same with the first color, an image processing is performed so that a grayscale of at least one of the first color and the second color is adjusted or a timing pulse of a near-infrared (NIR) fluorescence image signal is adjusted so that the second color is discontinuously implemented.

In an exemplary embodiment, the grayscale of the first color and the grayscale of the second color are adjusted so that a difference between the grayscale of the first color and the grayscale of the second color is equal to or greater than a specific threshold value.

In an another exemplary embodiment, the grayscale of the first color and the grayscale of the second color is relatively adjusted.

Other aspects and exemplary embodiments of the invention are discussed infra.

As described above, the device and the method for detecting the NIR fluorescence at the SLN according to the present invention have advantages as follows.

First, although the existing imaging system is used, it is possible to detect an SLN with high accuracy for a short period of time. Accordingly, it is possible to improve the accuracy in deciding the presence of cancer metastasis and to minimize the excision of an SLN.

Second, since it is unnecessary that the positions of focal surfaces of the NIR and VIS sensors should correspond to each other, it is unnecessary to correct a chromatic aberration in the laparoscope having an optical system, particularly an optical coupler.

Third, since the device and the method can be easily apply to existing laparoscopes, etc., it is possible to minimize additional cost consumption for device improvement.

The above and other features of the invention are discussed infra.

BRIEF DESCRIPTION OF THE DRAWINGS

The patent or application file contains at least, one drawing executed in color. Copies of this patent or patent application publication with color drawing (s) will be provided by the Office upon request and payment of the necessary fee.

The above and other features of the present invention will now be described in detail with reference to certain exemplary embodiments thereof illustrated the accompanying drawings which are given hereinbelow by way of illustration only, and thus are not limitative of the present invention, and wherein:

FIGS. 4A and 4B illustrate a preferred embodiment of the device according to the present invention, in which FIG. 4A shows an example applied to an ICG laparoscope, and FIG. 4B shows an example applied to an ICG videoscope;

Figure 1:
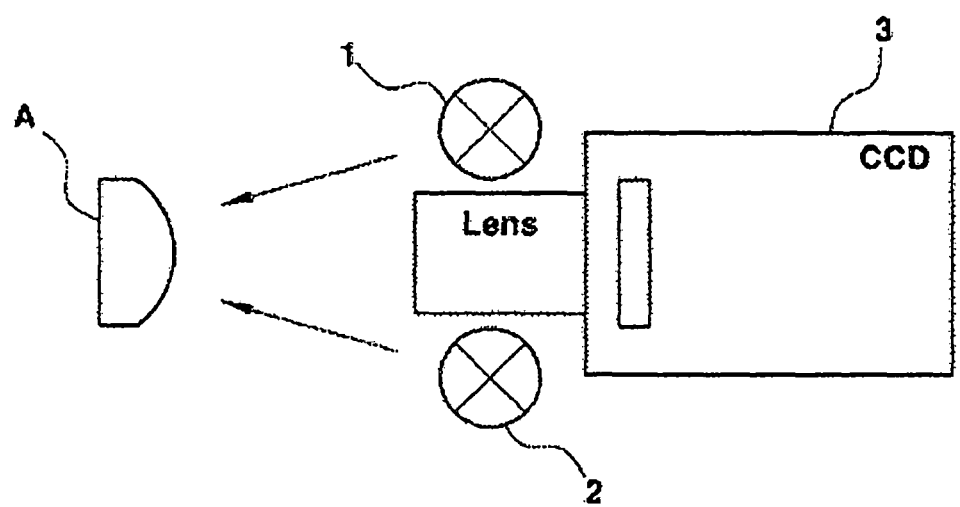
FIG. 1 schematically illustrates a conventional hyper eye medical system (HEMS) device for observing indocyanine green (ICG) fluorescent light.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

Hereinafter, a device for detecting near-infrared (NIR) fluorescence at a sentinel lymph node (SLN) according to an embodiment of the present invention will be described in detail with reference to the accompanying drawings.

Figure 2:
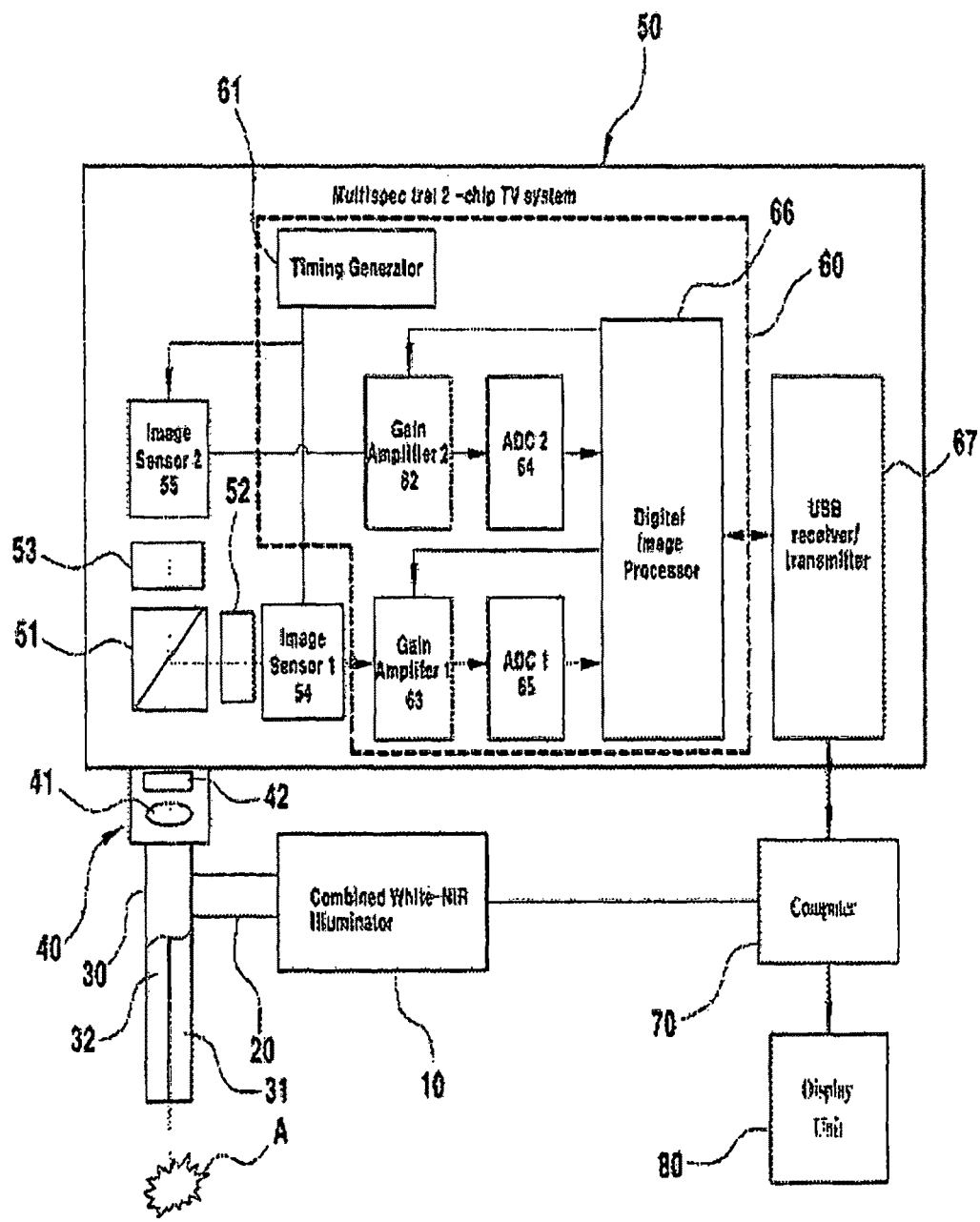
FIG. 2 illustrates a schematic configuration of a device for detecting near-infrared (NIR) fluorescence at a sentinel lymph node (SLN) according to the present invention.

FIG. 2 illustrates a schematic configuration of a device for detecting NIR fluorescence at an SLN according to the present invention. The device according to the present invention is provided with an optical analyzing assembly that faces an object to be observed at a part to be measured, and the optical analyzing assembly is configured according to the kind of imaging system.

Although it has been illustrated in FIG. 2 that a laparoscope is used as the imaging system, another imaging system such as a hard or soft endoscope, a camera or an operating microscope may be used as the imaging system.

Hereinafter, the case where the laparoscope is implemented as the optical analyzing assembly will be illustrated with reference to FIG. 2, and the device according to the present invention will be described in detail.

As shown in FIG. 2, the device according to the embodiment of the present invention is configured to include a combined white-NIR illuminator 10, a laparoscope 30, a multispectral image processing system 50, a computer 70 and a display unit 80.

In the device configured as described above, excitation light in an NIR wavelength band and white light, which are emitted from the combined white-NIR illuminator 10, is transmitted to an object A to be observed through an optical transmission module 31 included in the laparoscope 30 as the optical analyzing assembly by passing through an optical guide 20. Various biological objects to be observed may be considered as the object A to be observed, and a standard sample is used to be compared and observed with these objects. The combined white-NIR illuminator 10 provided with a lamp for emitting white light and a laser for emitting NIR light is used to obtain the combined white-NIR light.

Preferably, a white light source of the combined white-NIR illuminator 10 may be configured with a metal halide lamp or xenon lamp, and an NIR excitation light source of the combined white-NIR illuminator 10 may be configured with an NIR laser light source that emits light of 800±20 nm.

In this embodiment, the combined white-NIR illuminator integrally provided with the white light source and the NIR excitation light source has been described as an example, but the present invention is not limited to the form of the combined white-NIR illuminator. That is, any form of the may be used as long as the combined white-NIR illuminator provides the white light and the NIR excitation light to the object to be observed.

As such, the white light and the NIR excitation light from the combined white-NIR illuminator 10 are irradiated onto the object to be observed through the optical transmission module 31 of the laparoscope 30, and visible (VIS) reflection light, laser excitation light and NIR fluorescence are emitted from the object to be observed.

Figure 3:
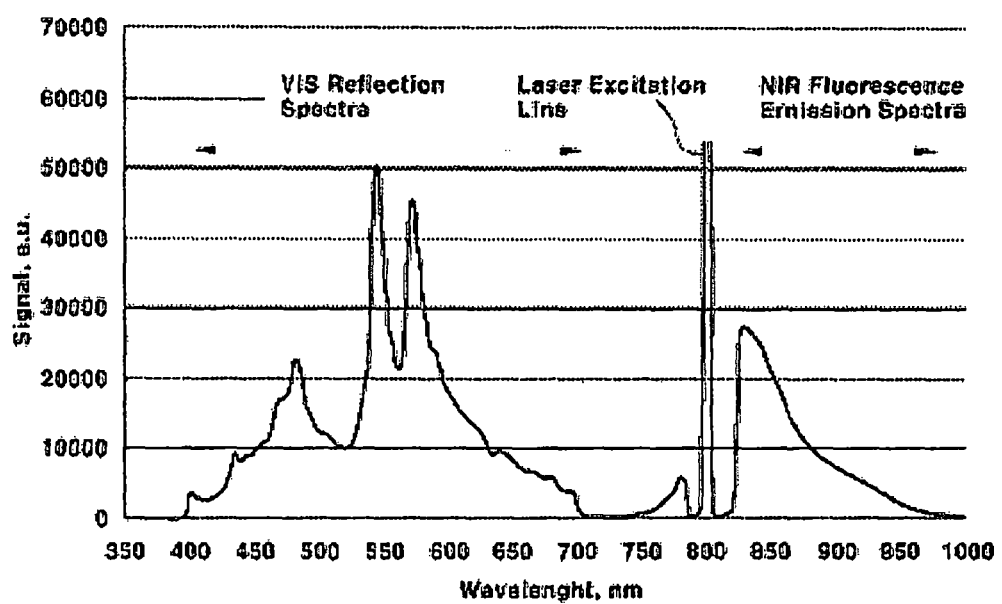
FIG. 3 illustrates wavelength ranges of visible (VIS) reflection light, laser excitation light and NIR fluorescence.

In relation to this, FIG. 3 schematically illustrates wavelength ranges of the VIS reflection light, the laser excitation light and the NIR fluorescence.

In this embodiment, the device is configured so that the light (the VIS reflection light+the NIR laser excitation light and fluorescence) emitted from the object to be observed can be transmitted to the multispectral image processing system 50. Hence, the device may be configured to include the laparoscope 30 and an optical adaptor 40 as shown in FIG. 2.

Thus, the light (the VIS reflection light+the NIR laser excitation light and fluorescence) emitted from the object to be observed is transmitted to the multispectral image processing system 50 through an optical imaging module 32 included in the laparoscope 30 and an optical coupler 41 included in the optical adaptor 40.

Meanwhile, in this embodiment, two image sensors for respectively processing an image in VIS and NIR regions are included as shown in FIG. 2. Hence, the multispectral image processing system 50 may be configured with a multispectral 2-chip TV system capable of simultaneously processing two images.

Here, a light-shielding filter 42 may be installed to prevent the laser excitation light in the NIR wavelength band from being penetrated into the multispectral image processing system 50 through the path of secondary lights reflected from the object to be observed and to allow light in the other wavelength bands to be transmitted therethrough.

Since the white reflection light for a background of the object to be observed and the fluorescence to be detected are required to be processed in the multispectral image processing system, the light-shielding filter 42 is used to shield a large amount of reflection excitation light to be detected.

Meanwhile, a beam splitter 51 may be installed in the multispectral image processing system 50. The beam splitter 51 splits the secondary light from the object to be observed into two lights, i.e., VIS and NIR. In addition, optical filters 52 and 53 are used to select one of spectra of the lights divided into two channels.

Here, a beam splitting prism using a prism may be used as the beam splitter. More preferably, a dichroic prism may be used as the beam splitter.

In the device according to this embodiment, an image sensor capable of sensing the wavelength of the split light is installed in each channel. That is, a color image sensor 54 and the optical filter 52 are installed in the VIS channel where the VIS is split from the beam splitter 51, and a monochrome image sensor 55 and an optical filter 53 are installed in the NIR channel where the NIR is split from the beam splitter 51.

The two sensors are controlled by the same video processing and control unit 60 including a common timing generator 61. A first gain amplifier 62 and a first analog/digital (A/D) converter 64 for the color image sensor 54 and a second gain amplifier 63 and a second A/D converter 65 for the monochrome image sensor 55 are installed in the video processing and control unit 60. As a result, a digital image including a white light image and an NIR fluorescence image is formed from these components of the video processing and control unit 60.

In relation to this, the device in this embodiment is configured to include a digital image processor 66 for analyzing and processing image signals collected in the multispectral image processing system and generating a VIS reflection light image signal and an NIR fluorescence image signal.

That is, the two-channel digital image processor 66 included in the video processing and control unit 60 generates a control signal for independently controlling amplification coefficients in the first and second gain amplifiers 62 and 63, and the control signal is required to perform an automatic gain control (AGC) condition. Here, if the AGC condition is set, the gain can be controlled so that the intensity of a predetermined reference light such as reflection excitation light or white reflection light.

The digital image processor 66 performs an operation in synchronization with the timing generator 61. The digital image processor 66 performs processing on a video signal and then transmits the video signal to computer 70 through a receiver/transmitter 67. The computer 70 performs image-processing on a VIS reflection light image and an NIR fluorescence image and makes the two images as a composite image to be displayed on a screen of the display unit 80.

Figure 4A:
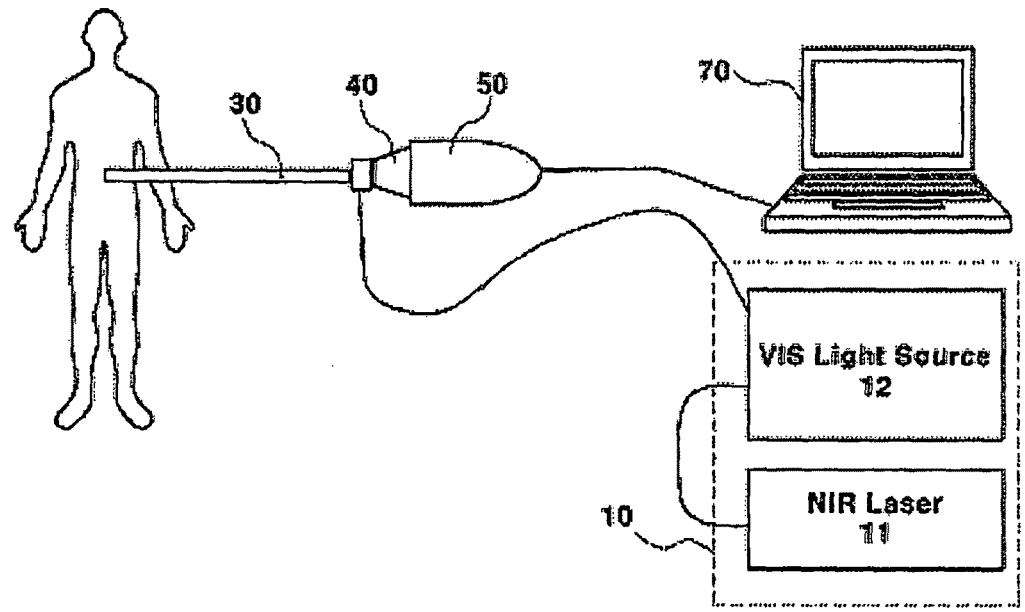
Figure 4B:
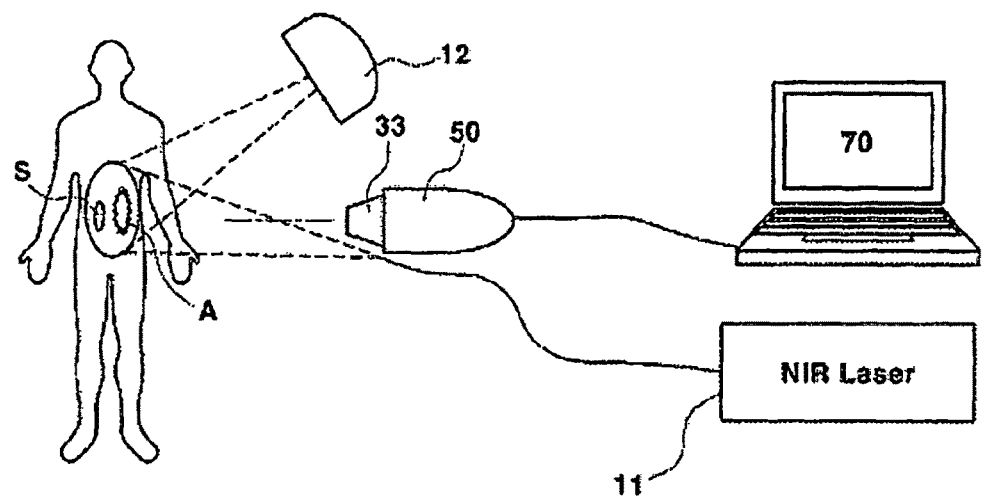

FIGS. 4A and 4B illustrate a specific embodiment of the device according to the present invention, in which FIG. 4A shows an indocyanine green (ICG) laparoscope, and FIG. 4B shows an ICG videoscope.

As shown in FIG. 4A, the device according to the present invention may be used in the form of an ICG laparoscope manufactured to detect an SLN in a human body. As shown in FIG. 4B, the device according to the present invention may be used in the form of an ICG videoscope manufactured to detect an SLN in an abdominal operation.

In each apparatus, a multispectral 2-chip TV system may be used as the multispectral image processing system as shown in FIG. 2, and an NIR laser 11 may be used as the NIR excitation light source. In addition, the device 12 includes a light source 12 for irradiating white light.

Particularly, in the ICG laparoscope, a combined VIS-NIR light source 10 including a VIS light source 12 as the white light source and a laser 11 as the NIR light source is used as the white light source in order to irradiate NIR excitation light and the white light at the same time.

In the ICG videoscope, a separated surgical lamp 12 and an NIR laser 11 are used rather than the combined VIS-NIR light source, and a camera lens 33 is used as the imaging system rather than the laparoscope.

Meanwhile, when image spectra in two wavelength bands of the VIS and the NIR are detected and recorded at the same time, a problem of chromatic aberration occurs in the imaging system designed and manufactured suitable for a VIS spectrum region. The chromatic aberration may be divided into an axial (longitudinal) chromatic aberration and a transverse (lateral) chromatic aberration, and a problem of the axial chromatic aberration is particularly important.

Figure 5A:
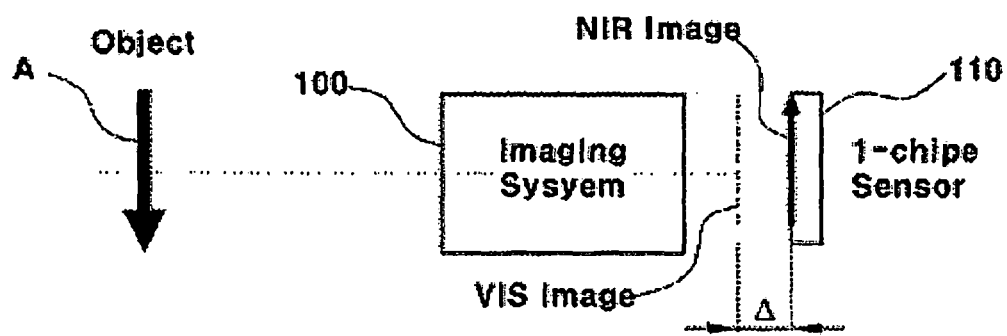
FIG. 5A conceptually illustrates a state in which a chromatic aberration occurs between VIS and NIR images, and FIG. 5B schematically illustrates a structure in which two image sensors are disposed to correct an axial chromatic aberration according to the preferred embodiment of the present invention.

Referring to FIG. 5A, the focus of a VIS spectrum image is relatively different by a value of A on an axis, as compared with that of an NIR spectrum image, which is referred to as the axial chromatic aberration.

In an embodiment of the present invention, an image sensor is installed in each of the VIS and NIR channels so as to correct such a chromatic aberration.

Figure 5B:
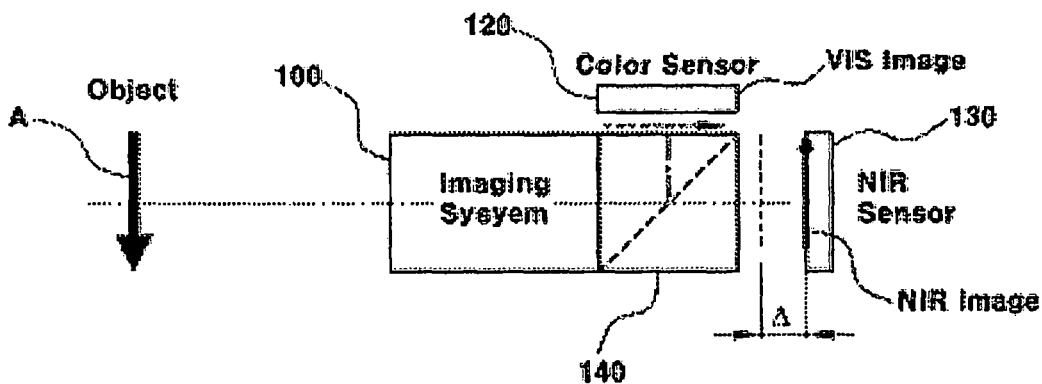

Particularly, as shown in FIG. 5B, a beam splitter for controlling an optical path according to wavelengths is mounted at a rear end of the imaging system. Preferably, the beam splitter uses a beam splitting prism that can split light by selectively transmitting or reflecting the light.

Thus, the beam splitter splits the light into VIS and NIR, and the split VIS and NIR are respectively incident onto the color image sensor and the NIR image sensor.

According to this embodiment, in order to correct the axial chromatic aberration, the position of the NIR image sensor is controlled to be relatively moved by a value of A, as compared with that of the color image sensor.

As a result, the axial chromatic aberration of each of the color and NIR image sensors having the controlled distance is corrected according to the moved position.

Thus, in the device according to this embodiment, the axial chromatic aberration is corrected without any increase in cost, caused as the separate VIS and NIR imaging system is used, and installation of a complicated optical module, so that it is possible to precisely control the focuses of the two images at the same time.

Meanwhile, the present invention provides a new method for simultaneously implementing NIR and VIS images and a device for detecting NIR fluorescence at an SLN, which is manufactured by the method.

In order to implement two images overlapped with each other using a general monitor, there occurs a problem how to distinguish an NIR fluorescence image belonging to a VIS reflection light image. In the present invention, a new method according to color contrast is used to easily distinguish the NIR fluorescence image.

In the color contrast, characteristics of a biological tissue having a yellow-red color tone in white reflection light are used.

Figure 6:
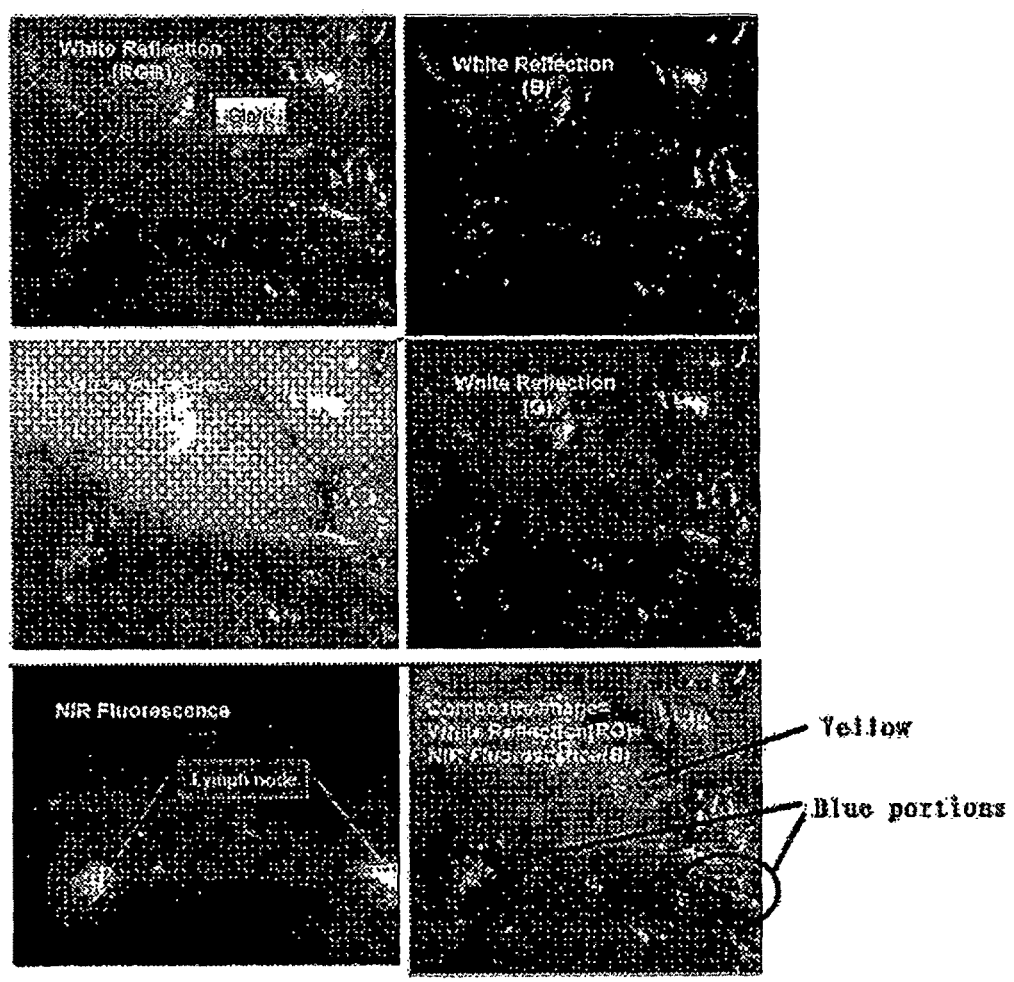
FIG. 6 illustrates images extracted with respect to the same part of a tissue, using the ICG laparoscope.

FIG. 6 shows images of a tissue obtained during observation using the ICG laparoscope. Here, red (R), green (G) and blue (B) signals of white reflection light are obtained after a white light image is separated in the channels R, G and B. In addition, an NIR fluorescence single image obtained in an NIR channel is shown in FIG. 6.

That is, FIG. 6 illustrates images with respect to the same part of the tissue, using the ICG laparoscope. In FIG. 6, the original image [White Reflection (RGB)] is shown in the RGB image, and the images obtained after the white reflection light image is separated in the R, G and B channels are respectively shown as R, B and B.

An image (NIR Fluorescence) obtained from the NIR fluorescence is also shown in FIG. 6, and a composite image of the VIS reflection light image and fluorescence image (VIS Reflection image+ICG Fluorescence Image) is finally shown in FIG. 6.

When comparing the images of FIG. 6, it can be seen that the unique shape of the biological tissue is hardly identified in the channel B. Here, a bright part of the object to be observed corresponds to a hot spot of intense light. That is, tissues in an actual human body can be mostly expressed with colors R and G, and it can be seen that the color B is not useful to distinguish the tissues.

Thus, in an embodiment of the present invention, an image of blue (B) is substituted as the NIR fluorescence image in the white reflection light, so that it is possible to implement the NIR fluorescence image together with the white reflection light.

Embodiment 1

In the configuration of a composite image under the condition of a mode in which white reflection light and ICG fluorescence are combined (Reflected White Image+ICG Fluorescence Image), the NIR image fluorescence image is selected other than the image of blue (B) image in a reflection light image background of red (R) and green (G).

The blue obtained from the white reflection light is not a characteristic element for the image of a tissue, and thus the SLN displayed by the NIR fluorescence is easily distinguished from other tissues. In addition, the SLN is distinguished from hot spots shown in the white reflection light. The white reflection light image forming the image background in the composite image is expressed by only the channels of red (R) and green (G). Since the hot spot has no blue, the hot spot is shown as yellow. Meanwhile, the NIR fluorescence image is shown as blue (B).

That is, a composite image output using the white reflection light (RG) and the NIR fluorescence (B) is shown at the right lower end of FIG. 6. In the composite image, the tissue is expressed as an image background by the channel of red (R) and green (G), and the hot spot is expressed as yellow (R+G). The NIR fluorescence image is expressed as blue (blue portions) through the channel of B.

Accordingly, it is possible to easily observe an SLN related to the NIR fluorescence together with the exact structure of a tissue.

A method for detecting NIR fluorescence at an SLN according to this embodiment will be described in connection with the device shown in FIG. 2. First, if a color image (white reflection light) and a monochrome image (fluorescence) are collected through a device such as a laparoscope, the color and monochrome images are transmitted to the multispectral image processing system through the optical coupler, etc. Information on the transmitted color and monochrome images is divided into VIS and NIR regions through the beam splitter, and then converted into electrical signals through the two image sensors.

Each of the signals respectively converted through the image sensors passes through the gain amplifier and the A/D converter. Then, the signals are respectively processed as a VIS reflection light image signal and an NIR fluorescence image signal in the digital image processor. In this embodiment, the white reflection light and the NIR fluorescence are respectively formed with an image of RG and an image of B through the digital image processor. In this case, the synchronization is performed by the timing generator 61 in the process of forming the images, and thus the fluorescence image signal is simultaneously obtained together with a background caused by white light so that it is possible to obtain VIS reflection light and NIR fluorescence image signals for implementing a composite image.

The obtained are transmitted to the computer through the transmitter/receiver, and the computer combines the transmitted VIS reflection light and NIR fluorescence image signals, thereby implementing a composite image through the display unit.

Figure 7:
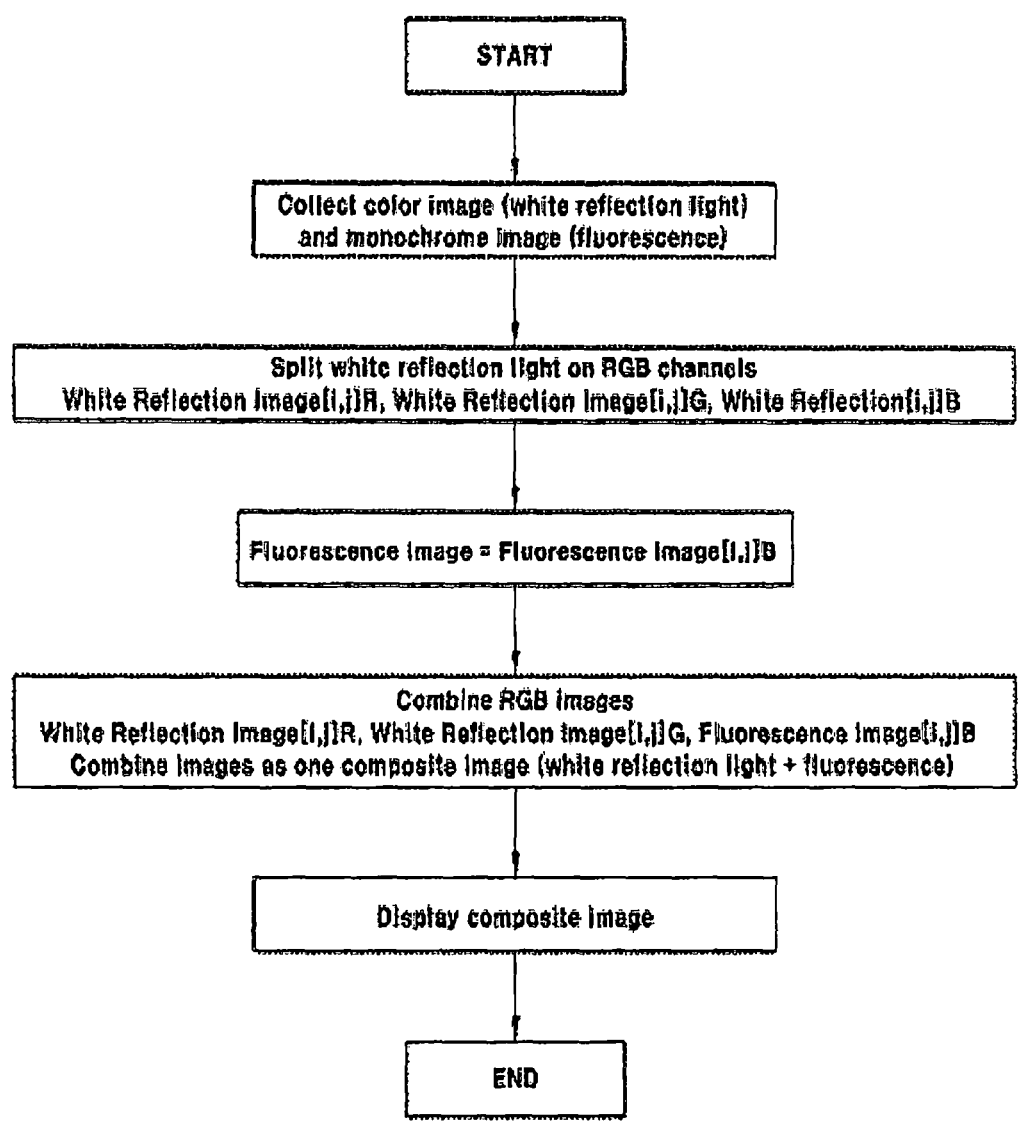
FIG. 7 is a block diagram sequentially illustrating a process of forming a composite image in which an NIR fluorescence image is overlapped with a white reflection light image background by using an NIR fluorescence signal other than blue (B) in white reflection light according to an embodiment of the present invention.

In relation to this, FIG. 7 is a block diagram sequentially illustrating a process of forming a composite image in which an NIR fluorescence image is overlapped with a white reflection light image background by using an NIR fluorescence signal other than blue (B) in white reflection light.

As shown in FIG. 7, the color image (white reflection light) and the monochrome image (fluorescence) are collected, and the collected white light image is split on the RGB channels, thereby obtaining signals of R (White Reflection Image[i, j]R), G (White reflection image[i, j]G) and B (White reflection image[i, j]B) with respect to white light.

Next, the signal of the fluorescence image is generated as a signal of B (Fluorescence Image[i, j]B), and a composite image is generated using the signal of B together with signals of R and G, thereby outputting the composite image.

That is, in this embodiment, when the composite image is generated, the blue (B) of the NIR fluorescence is displayed in the pixel where the NIR fluorescence is detected, and the red (R) and green (G) of the white reflection light are displayed in the pixel where the NIR fluorescence is not detected.

Meanwhile, unlike Embodiment 1, in another preferred embodiment, the amplitudes of the blue (B) of the white reflection light and the NIR fluorescence are relatively compared. Thus, one of both, of which intensity is relatively strong, is selected for each pixel, thereby implementing a composite image.

Basically, since the intensity of the blue (B) of the white reflection light is different from that of the NIR fluorescence, the comparison between the absolute amplitudes of the blue (B) of the white reflection light and the NIR fluorescence is not appropriate in detecting the position of an SLN. Therefore, the method of relatively comparing the amplitudes of the blue (B) of the white reflection light and the NIR fluorescence may be used in the preferred embodiment of the present invention.

For example, since the intensity of the NIR fluorescence signal is much smaller than that of the white reflection light, the NIR fluorescence signal may be amplified by multiplying the NIR fluorescence signal by a predetermined gain, and the amplitude of the amplified NIR fluorescence signal may be then relatively compared with that of the white reflection light.

Embodiment 2

In this embodiment, the intensities of the blue (B) of the white reflection light and the NIR fluorescence are relatively compared for each pixel, so that one of both the blue (B) of the white reflection light and the NIR fluorescence, of which intensity is strong, is selected and output as the blue (B).

Thus, when the intensity of the blue (B) of the white reflection light is stronger than that of the NIR fluorescence, the blue (B) of the white reflection light is selected, thereby implementing RGB colors of the white reflection light together with the red (R) and the green (G). When the intensity of the NIR fluorescence is stronger than that of the blue (B) of the white reflection light, the NIR fluorescence is selected as the blue (B). Hence, the NIR fluorescence is output as a composite image together with the red (R) and the green (G) of the white reflection light.

Figure 8:
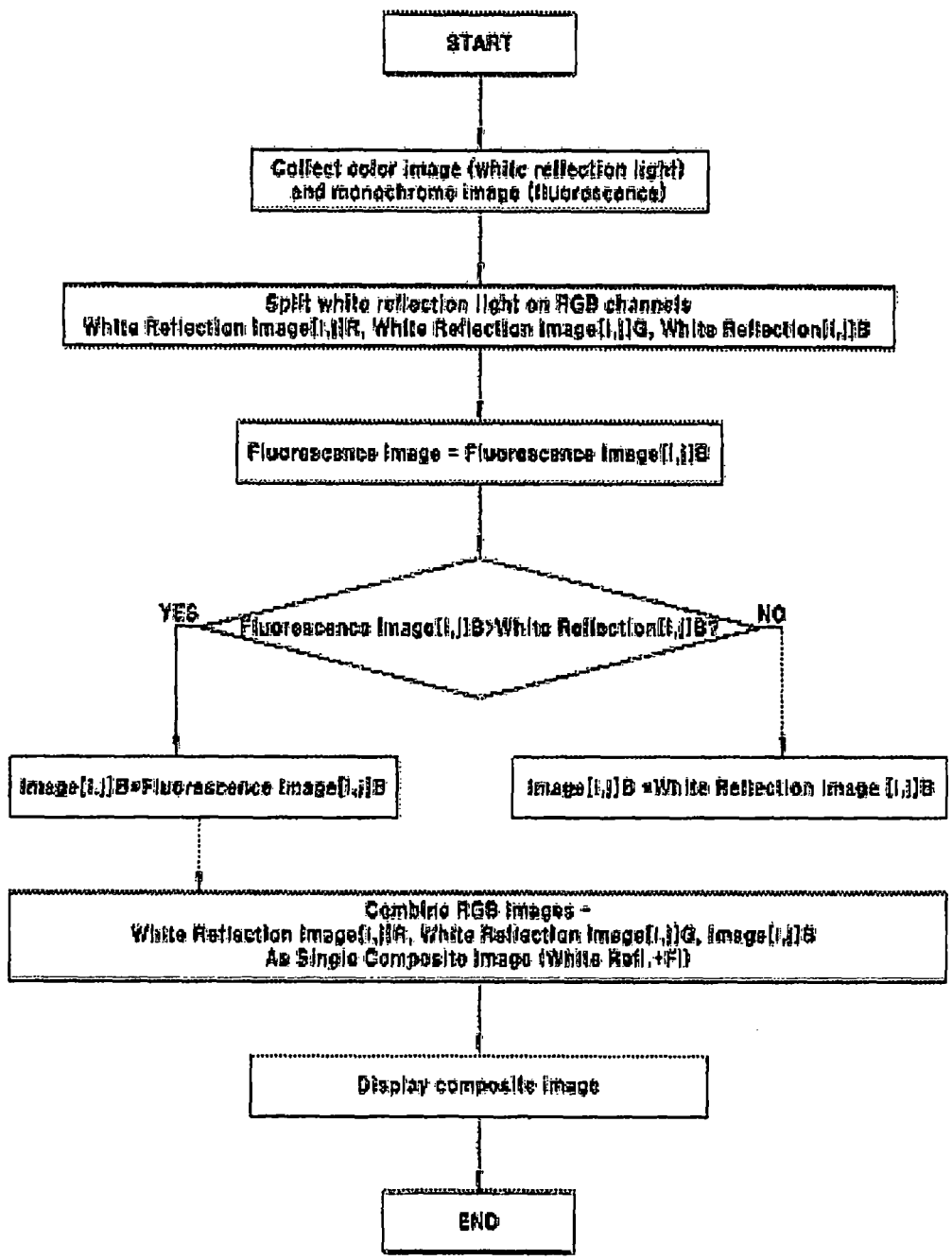
FIG. 8 is a block diagram illustrating an example in which the blue (B) is selectively output by comparing the intensity of the blue (B) of the white reflection light and the intensity of the NIR fluorescence according to an embodiment of the present invention.

FIG. 8 is a block diagram illustrating an example in which the blue (B) is selectively output by comparing the intensity of the blue (B) of the white reflection light and the intensity of the NIR fluorescence.

As shown in FIG. 8, when the signal intensity of the NIR is stronger than that of the VIS in an image pixel expressing a color, the pixel emitting the blue of the white reflection light is replaced with the pixel emitting the NIR fluorescence, and thus only the NIR fluorescence image signal is displayed as the blue (B). On the contrary, the blue (B) image signal of the white reflection light is displayed, together with the red (R) and green (G) signals of the white reflection light, as a composite color in a corresponding pixel. Thus, the corresponding pixel is displayed as the blue (B).

Figure 9:
FIG. 9 illustrates a composite image obtained from the device according to the embodiment of FIG. 8.

The composite image obtained according to this embodiment is shown in FIG. 9. That is, in FIG. 9, each pixel corresponding to the condition when the intensity of an NIR signal exceeds that of a blue light signal displays a signal obtained in the channel of the NIR fluorescence image other than the channel of blue (B) in the white reflection light image. Thus, it can be seen that the signal obtained in the channel of the NIR fluorescence image is displayed as blue (blue portions) at the left and right sides of FIG. 9.

In this case, the hot spot shown in the white reflection light is shown as white as the original color at the early stage, and the color tone of the tissue is not changed at a part where the intensity of the NIR signal is weaker than that of the blue signal in the white reflection light.

Meanwhile, in the device and the method according to the present invention, the SLN is more exactly identified through an additional process of analyzing a composite image provided to the display unit.

Particularly, in the present invention, a standard sample may be used to more exactly identify the SLN.

Specifically, in the present invention, the ICG is basically used as a contrast medium to distinguish the SLN from non-SLNs, and the SLN is distinguished from the non-SLNs through a difference in intensity between fluorescence signals generated from the ICG when laser excitation light is irradiated. The intensity of the fluorescence signal depends on several elements. That is, the intensity of the fluorescence signal depends on the intensity of light irradiated onto the object to be observed, the sensitivities of VIS and NIR detection sensors, parameters (gain and shutter) of the video processing and control unit, the measurement distance between the device and the object to be observed, and the like. Among these elements, it is difficult to control the measurement distance. This is because the measurement distance is frequently changed due to histological characteristics of the object to be observed, close observation of a required part to be observed, or the like.

Therefore, a fluorescence standard sample having a fluorescence intensity similar to that of the SLN is required to exactly identify the SLN. The fluorescence standard sample may be prepared by basically using an ICG solution in which serum of blood or albumin is added. The ICG solution is generally used as a fluorescence activator for increasing fluorescence intensity. As the activator, other materials other than an organic material which can increase fluorescent intensity and more stably maintain fluorescence may be used. When a beauty shampoo is used as a candidate of the activator in an experiment performed by this research, it can be seen that the fluorescence intensity of the ICG solution in a sealed plastic container is maintained without any change for at least one month. When the ICG solution with a predetermined concentration is used, the fluorescence intensity of the standard sample may be controlled similarly to that of the SLN.

The method of identifying the SLN may be divided into two different methods depending on whether the standard sample is disposed at a side of the object to be observed or not.

Figure 10:
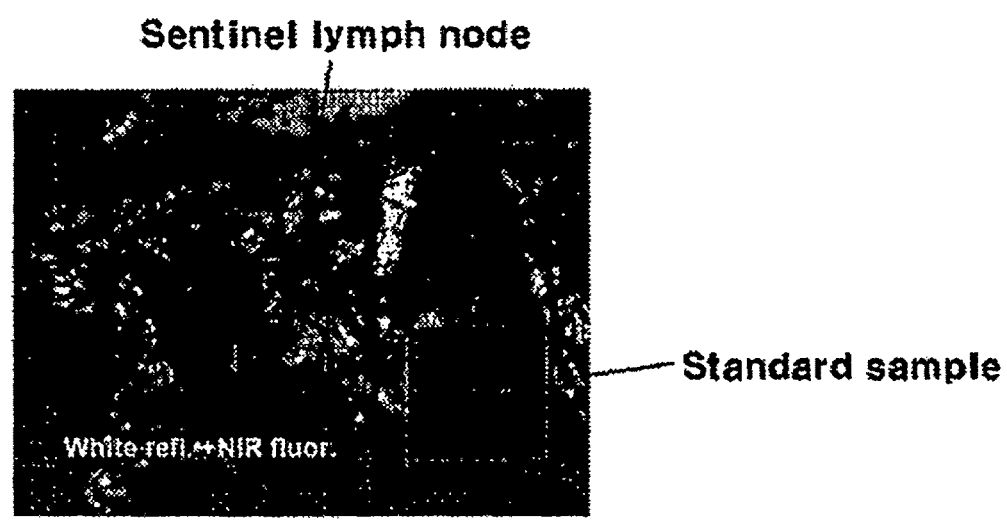
FIG. 10 illustrates a composite image obtained in a state in which a standard sample is disposed at a side of an SLN that is an object to be observed.

First, when considering that the standard sample is disposed at a side of the object to be observed, the standard sample may be disposed at a side of an SLN to be observed in order to compare the fluorescence intensity of the standard sample with that of a part to be operated. The example in which the standard sample is disposed at a side of the SLN that is an object to be observed is shown in FIG. 10.

In this case, the comparison between the intensity of a fluorescence signal of the object to be observed (lymph node) and the intensity of a fluorescence signal of the standard sample may be performed with the naked eyes through a monitor or by quantitative estimation. If the fluorescence intensity of the lymph node (FI Lymph Node) is greater than that of the standard sample (FI Standard Sample), the lymph node that is the object to be observed is an SLN. If the fluorescence intensity of the lymph node (FI Lymph Node) is smaller than that of the standard sample (FI Standard Sample), the lymph node is a non-SLN. Here, the fluorescence intensity of the lymph node means a fluorescence signal of the object to be observed.

Figure 11:
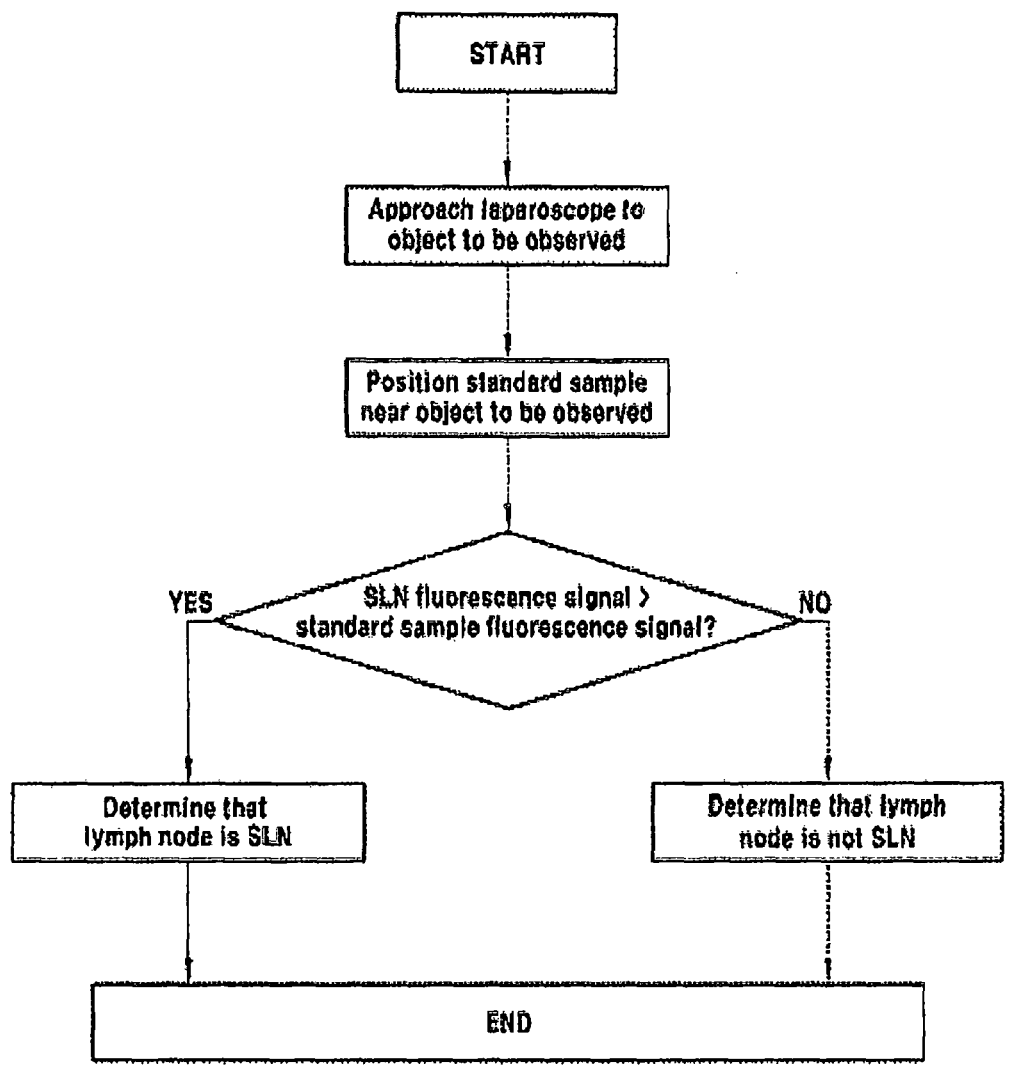
FIG. 11 is a block diagram illustrating a method of identifying an SLN when the standard sample is positioned near the object to be observed.

In relation to this, FIG. 11 is a block diagram illustrating a method of detecting an SLN when the standard sample is positioned near the object to be observed.

That is, referring to the block diagram of FIG. 11, the laparoscope is approached to the object to be observed, and the standard sample is then positioned near the object to be observed. Subsequently, the intensity of the fluorescence signal of the lymph node that is the object to be observed is compared with that of the fluorescence signal of the standard sample, and it is Determined whether the lymph node is an SLN, based on the compared result.

Meanwhile, it is considered when the standard sample is not disposed at a side of the object to be observed.

The comparison between the intensity of the fluorescence signal of the lymph node and the intensity of the fluorescence signal of the standard sample is a direct method.

However, when the standard sample is not used, a change in measurement distance from the object to be observed may be automatically calculated using a white reflection light signal.

Figure 12:
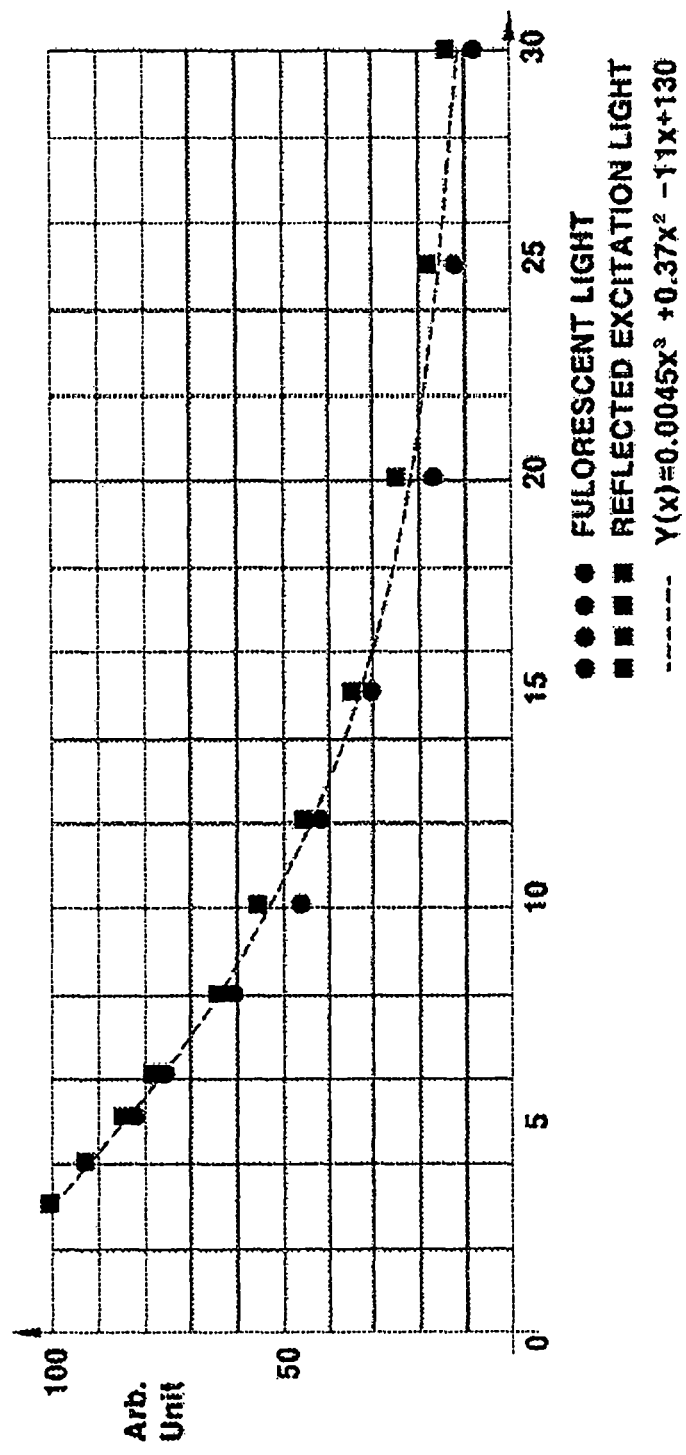
FIG. 12 is a graph illustrating changes in fluorescence and reflection light signals according to a change in measurement distance from the object to be observed.

FIG. 12 is a graph illustrating changes in fluorescence and reflection light signals according to a change in measurement distance from the object to be observed. Referring to FIG. 12, it can be seen that the intensities of the reflection excitation light and the fluorescence are decreased at the almost same rate according to the measurement distance of the object to be observed.

Therefore, if the parameters (gain and shutter) are automatically controlled so that reference light is always constant, using the reflection excitation light or white reflection light as the reference light, it is possible to obtain the same intensity of the fluorescence, regardless of the distance.

That is, when considering the device of FIG. 2, the parameters in the first and second gain amplifiers are automatically controlled so that the reference light signal is constant in the digital image processor, so that it is possible to continuously obtain a fluorescence signal with the same intensity, regardless of the distance.

In relation to this, in this embodiment, white reflection light is used rather than reflection excitation light so as to correct the measurement distance. In this case, a signal generated from light of red (R), green (G) or blue (B) may be used as the reference light. Preferably, an optical signal generated from the channel R that receives less influence from structural characteristics of the tissue to be observed may be used as the reference light.

Figure 13:
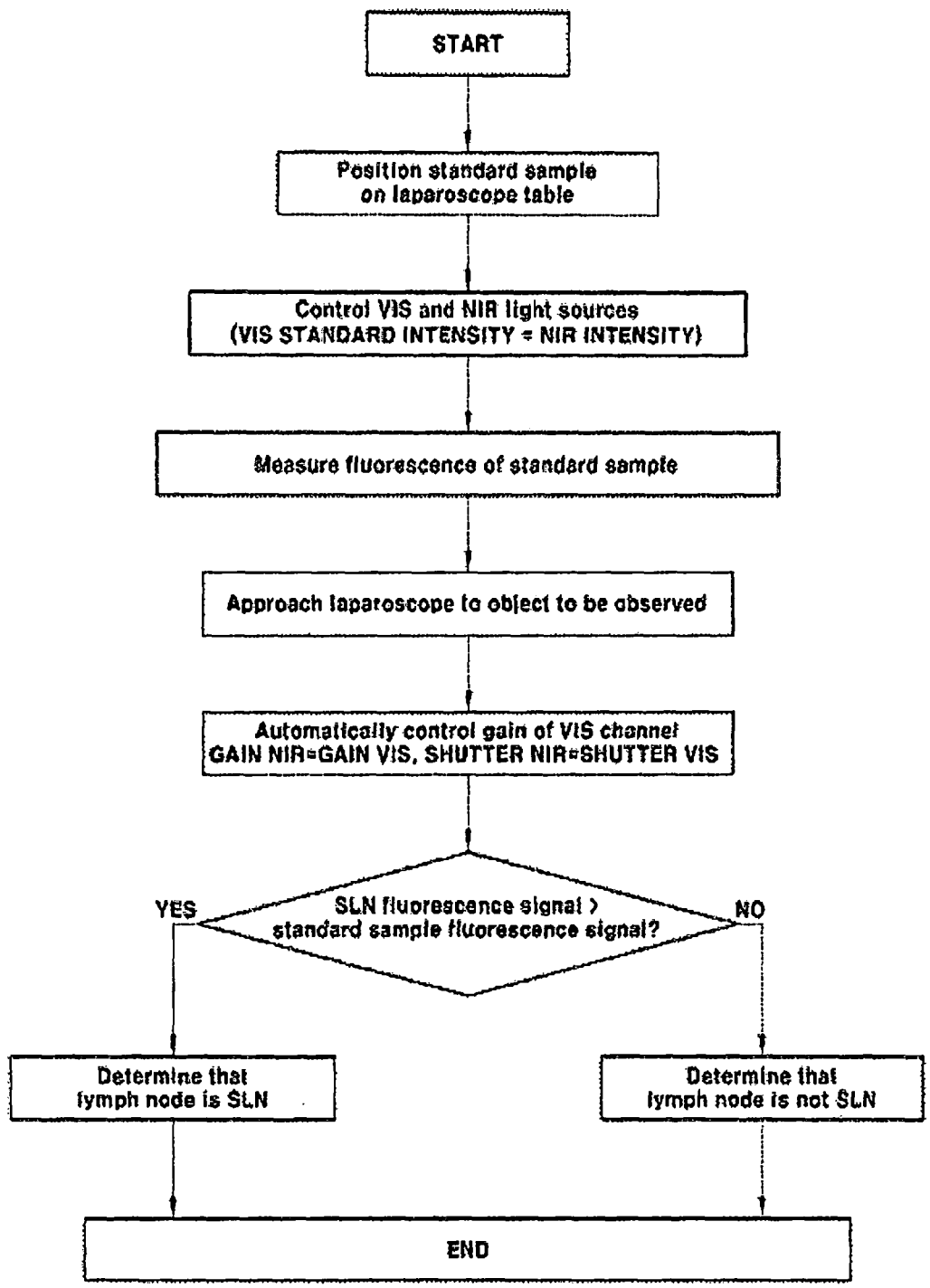
FIG. 13 is a block diagram illustrating a method of identifying an SLN when the standard sample is not disposed at the side of the object to be observed.

When the standard sample is not disposed at the side of the object to be observed, a process of identifying an SLN is shown in FIG. 13.

First, a standard sample is disposed, and a correcting operation of the system is performed based on measurement values of VIS and NIR signals with respect to the standard sample. The proportional expression according to the distance between white and NIR standard samples is performed by measuring a light intensity of each standard sample, and a diffused reflection value is measured.

After the laparoscope is inserted into a human body, the parameters (gain and shutter) are changed suitable for the intensity of white light, and accordingly, the signal of the white light channel (VIS light channel) is automatically amplified and controlled. In this case, the parameters are equally changed in not only the white light channel but also an NIR channel, thereby removing an error of the measurement distance.

If an increase in fluorescence at a lymph node is observed, the fluorescence intensity of the lymph node is measured.

If the fluorescence intensity of the lymph node to be observed is higher than that of the standard sample, it is determined that the lymph node is an SLN. If the fluorescence intensity of the lymph node to be observed is lower than that of the standard sample, it is determined that the lymph node is a non-SLN.

Meanwhile, the detection of the fluorescence signal at the SLN may be considered through a temporal modulation method together with the color contrast method.

Figure 14:
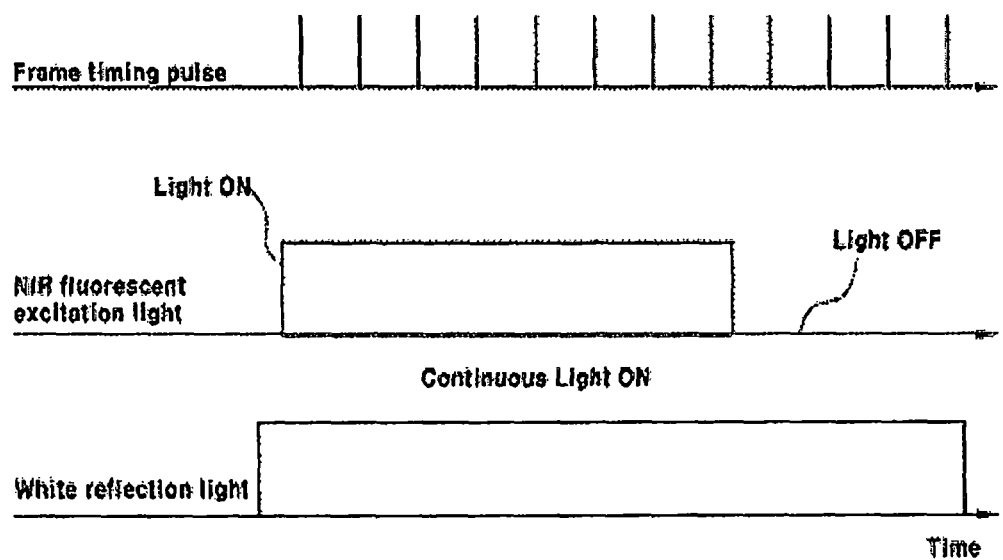
FIG. 14 illustrates a continuous white reflection light signal, a frame rate of a light detection sensor and a periodical pulse signal of asynchronous NIR fluorescence excitation light.

FIG. 14 illustrates a continuous white reflection light signal, a frame rate of a light detection sensor and a periodical pulse signal of asynchronous NIR fluorescence excitation light.

Referring to FIG. 14, in the temporal modulation method, the light irradiation of the white light source is continuously performed, and thus the white reflection light is continuously output. Meanwhile, the NIR fluorescence is configured to be changed into a pulse mode having a frequency much smaller than the frame rate of the TV system. Thus, the NIR excitation light has a discontinuous light irradiation output. In this case, it is unnecessary to allow the modulation rate of laser irradiation to be synchronized with the frame rate of the TV system.

Thus, the NIR fluorescence image is periodically glittered in the VIS background image caused by the continuously output white reflection light, so that it is possible to easily identify the NIR fluorescence image.

The temporal modulation method may be independently used. Preferably, the temporal modulation method is used together with the color contrast method of Embodiment 1 or 2, so that it is possible to easily detect a fluorescence signal from the SLN.

Embodiment 3

Through the temporal modulation method, the output mode of continuous laser is changed into a pulse mode having a repetition rate of 1 to 2 Hz that is much smaller than 15 Hz that is the frame rate of the light detection sensor of the TV system used in the endoscope.

Thus, the NIR image in the continuous VIS image background is periodically glittered due to the pulse mode.

In this embodiment, the temporal modulation method is performed separately from the color contrast method, and thus the VIS image maintains perfect colors (RGB). On the other hand, when the temporal modulation method is used together with the color contrast method of Embodiments 1 and 2, the blue (B) can be replaced in the NIR fluorescence image, and thus the VIS image may be formed with the red (R), the green (G), and the NIR fluorescence image. Alternatively, when the intensity of a blue (B) light signal is greater than that of the NIR fluorescence image, the VIS image may be perfectly formed with the red (R), the green (G) and the blue (B).

Figure 15A:
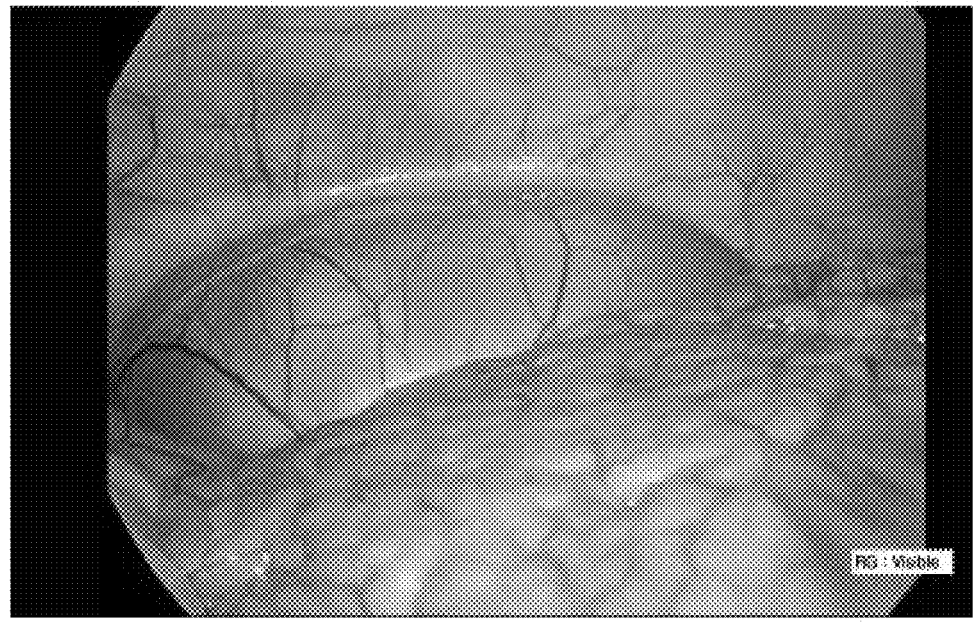
FIGS. 15A to 15C are images obtained by imaging a biological tissue (a tissue inside a human body) using an apparatus for detecting near-infrared fluorescence according to an embodiment of the present invention.
Figure 15B:
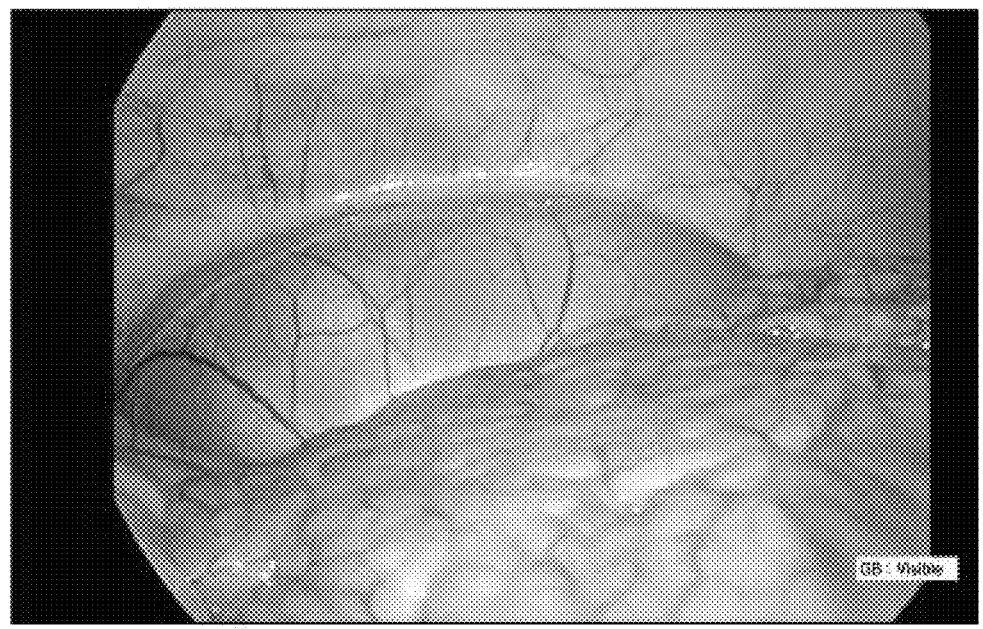
Figure 15C:
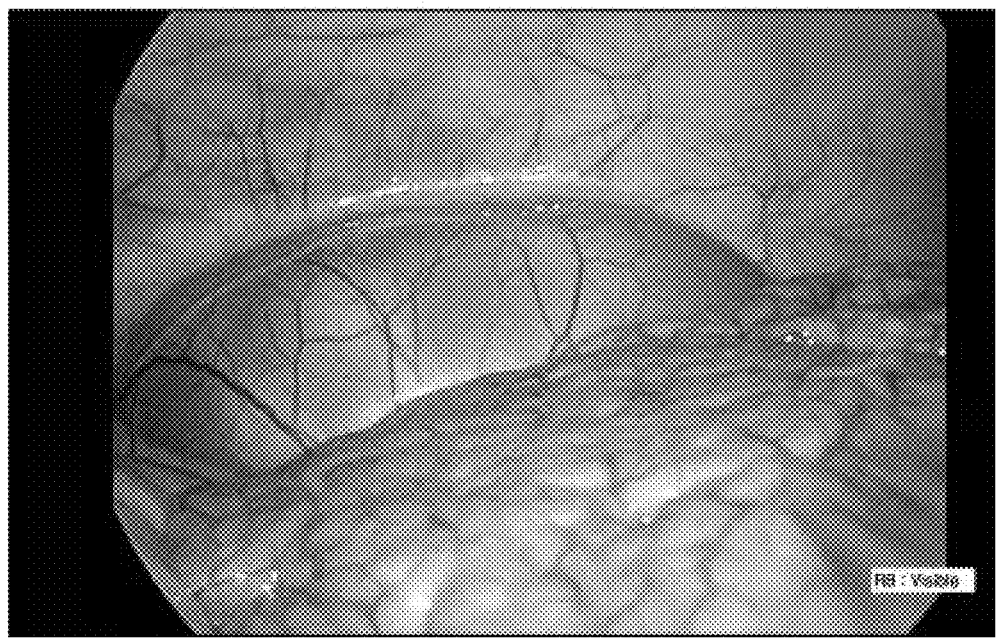
Figure 16A:
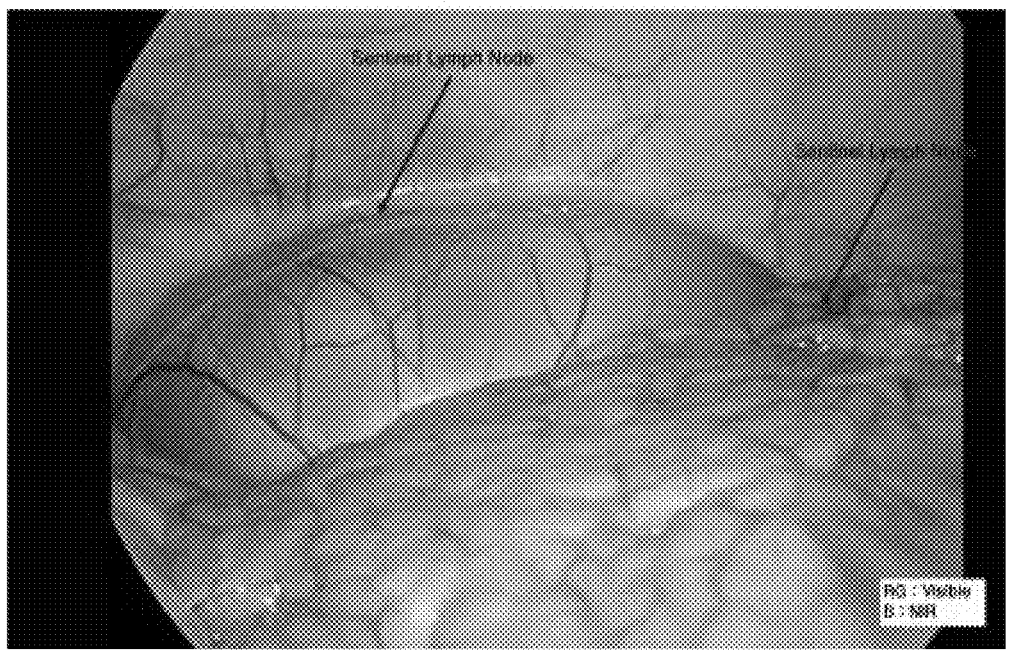
FIGS. 16A to 16C are images obtained by imaging the biological tissue (a tissue inside the human body) and a sentinel lymph node in the tissue using the apparatus for detecting near-infrared fluorescence according to an embodiment of the present invention.
Figure 16B:
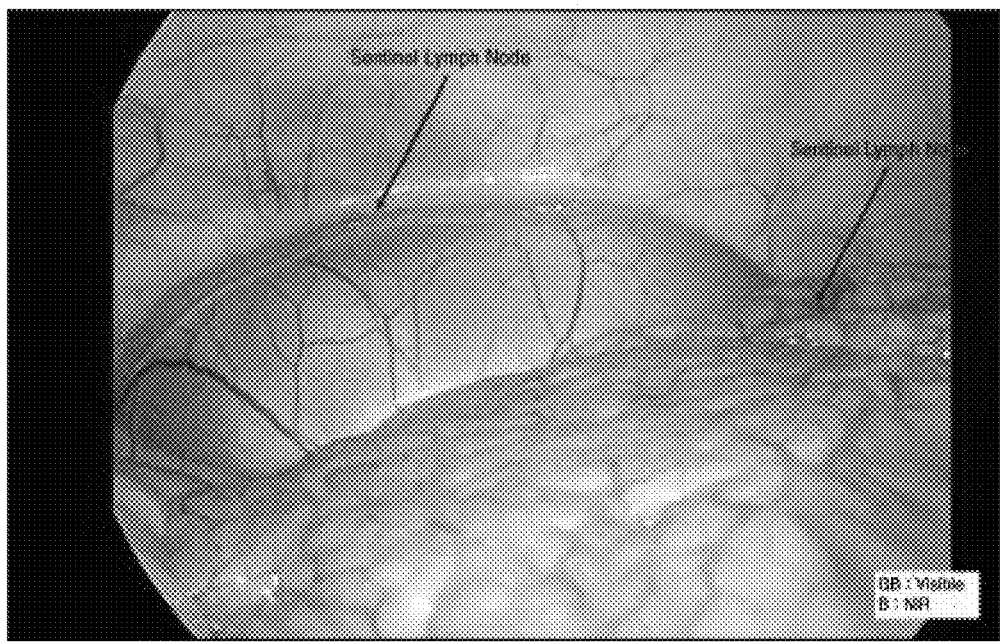
Figure 16C:
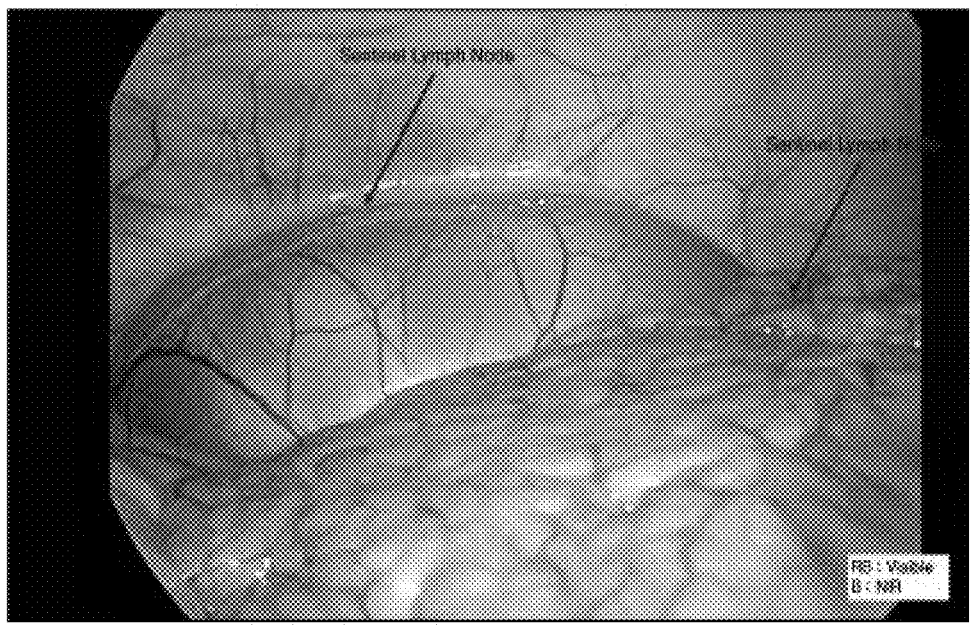

FIGS. 15A to 15C are images obtained by imaging a biological tissue (a tissue inside a human body) using an apparatus for detecting near-infrared fluorescence according to an embodiment of the present invention, FIGS. 16A to 16C are images obtained by imaging the biological tissue (a tissue inside the human body) and a sentinel lymph node in the tissue using the apparatus for detecting near-infrared fluorescence according to an embodiment of the present invention.

More specifically, FIG. 15A shows an image obtained by performing image processing in the multispectral image processor 50 so that the white reflection light (Visible) obtained from a living tissue is expressed by only red color (R) and green color (G), FIG. 15Bb shows an image obtained by performing image processing in the multispectral image processor 50 so that the white reflection light (Visible) obtained from a living tissue is expressed by only green color (G) and blue color (B), FIG. 15C shows an image obtained by performing image processing in the multispectral image processor 50 so that the white reflection light (Visible) obtained from a living tissue is expressed by only red color (R) and blue color (B).

Also, FIG. 16A shows an image obtained by performing image processing so that a sentinel lymph node of the living tissue shown in FIG. 15A is seen by blue color (B), using near-infrared fluorescence, FIG. 16B shows an image obtained by performing image processing so that a sentinel lymph node of the living tissue shown in FIG. 15B is seen by blue color (B), using near-infrared fluorescence, FIG. 16C shows an image obtained by performing image processing so that a sentinel lymph node of the living tissue shown in FIG. 15C is seen by blue color (B), using near-infrared fluorescence.

Referring to FIG. 15A to 15C, in the case of expressing the living body tissue by combining just only two colors among red color (R), blue color (B) and green color (G), it is seen as a distorted color not an inherent color thereof. In this case, even though the living body tissue is shown by a distorted combination of red color (R) and green color (G) or blue color (B) and green color (G) to blue color (B), if the sentinel lymph node is shown by blue color (B) using near-infrared fluorescence, this expression method is suitable because the living body tissue and the sentinel lymph node can be easily distinguished from each other as shown in FIG. 16A and FIG. 16.

However, referring to FIG. 16C, if the living body tissue is shown by a distorted combination of red color (R) and blue color (B) and the sentinel lymph node is shown by blue color (B) using near-infrared fluorescence, the living body tissue and the sentinel lymph node cannot be easily distinguished from each other. In such a case, a position of the sentinel lymph node cannot be accurately grasped so that it may be difficult to confirm a cancer metastasis using the sentinel lymph node.

As shown in FIG. 16C, it is difficult to distinct the living body tissue and the sentinel lymph node according to an expressed color of the living body tissue when the sentinel lymph node is expressed by only blue color (B) using near-infrared fluorescence, as well as expressing by only red color (R) or only green color (G).

In order to solve the above problems, an apparatus for detecting the infrared fluorescence according to another embodiment of the present invention implements images by performing image processing a biological tissue or a sentinel lymph node in the tissue in the same manner as in the following FIG. 17 and FIG. 18A to FIG. 18C.

Figure 17:
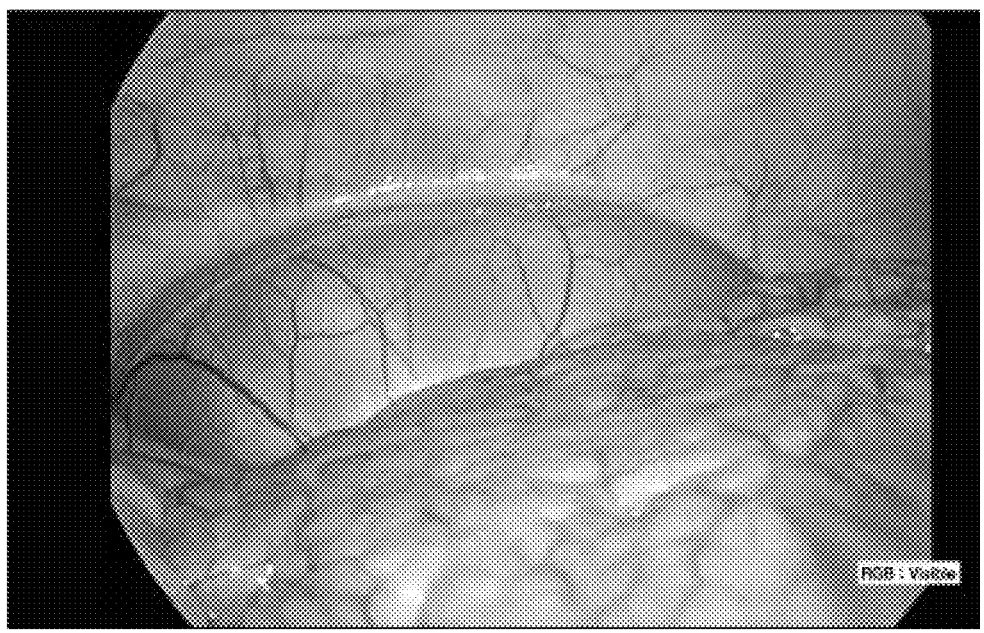
FIG. 17 is an image obtained by imaging a biological tissue (a tissue inside a human body) using an apparatus for detecting near-infrared fluorescence according to an another embodiment of the present invention.
Figure 18A:
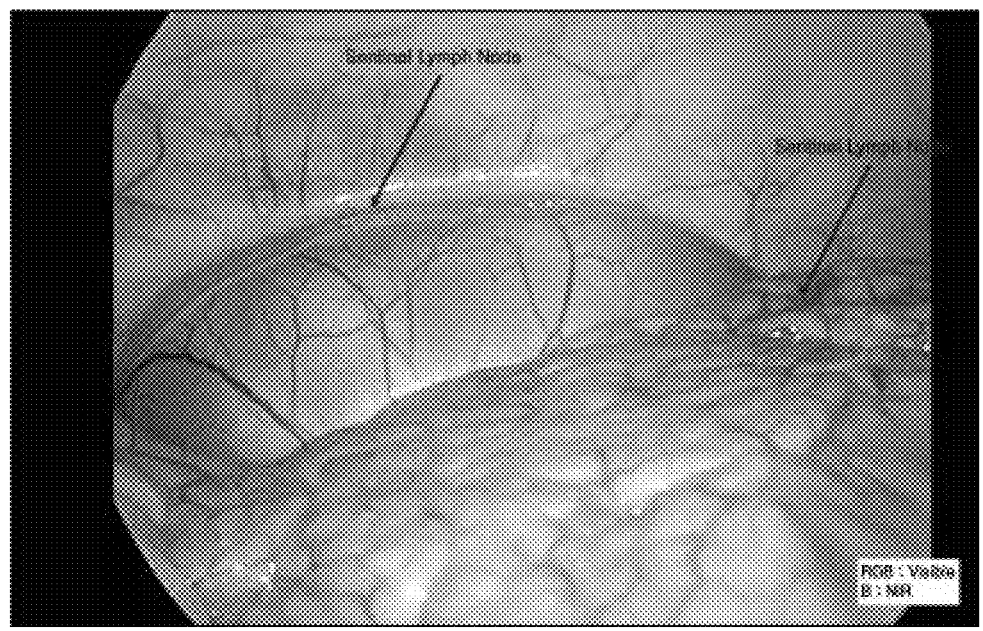
FIG. 18A to 18C are images obtained by imaging the biological tissue (a tissue inside the human body) and a sentinel lymph node in the tissue using the apparatus for detecting near-infrared fluorescence according to an another embodiment of the present invention.
Figure 18B:
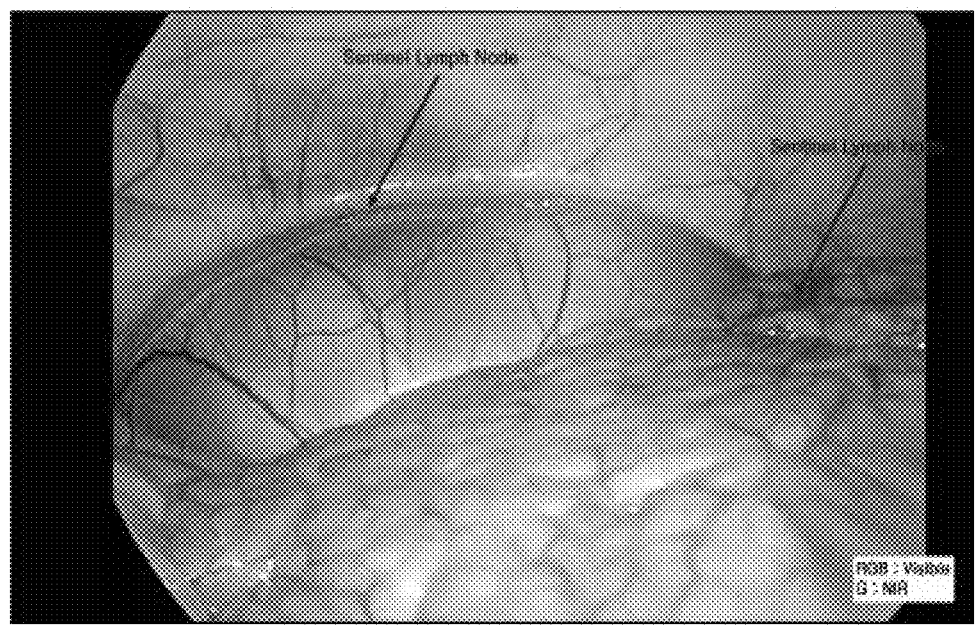
Figure 18C:
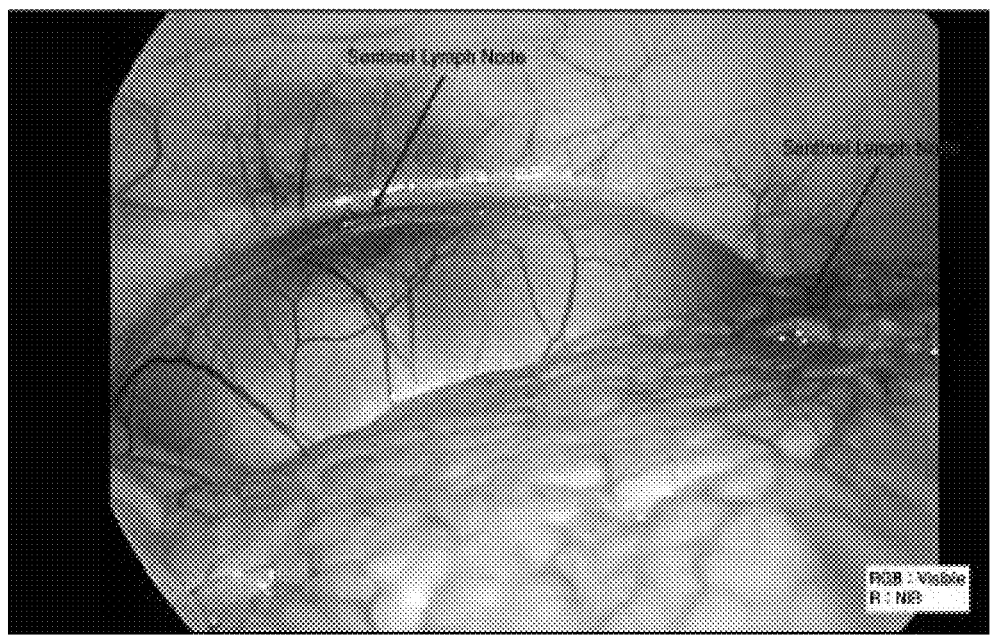

FIG. 17 is an image obtained by imaging a biological tissue (a tissue inside a human body) using an apparatus for detecting near-infrared fluorescence according to an another embodiment of the present invention, FIG. 18A to 18C are images obtained by imaging the biological tissue (a tissue inside the human body) and a sentinel lymph node in the tissue using the apparatus for detecting near-infrared fluorescence according to an another embodiment of the present invention.

More specifically, FIG. 17 shows an image obtained by performing image processing in the multispectral image processor 50 so that the white reflection light (Visible) obtained from the living tissue is expressed by a combination of red color (R), green color (G) and blue color (B). Also, FIG. 18A shows an image obtained by performing image processing so that a sentinel lymph node of the living tissue shown in FIG. 17 is seen by blue color (B), using near-infrared fluorescence. FIG. 18B shows an image obtained by performing image processing so that a sentinel lymph node of the living tissue shown in FIG. 17 is seen by green color (G), using near-infrared fluorescence. FIG. 18C shows an image obtained by performing image processing so that a sentinel lymph node of the living tissue shown in FIG. 17 is seen by red color (R), using near-infrared fluorescence.

As shown in FIG. 17, if the living tissue is expressed by a first color using all of red color (R), blue color (B) and green color (G), the living tissue can be expressed by the inherent color without distorting color thereof. In such a case, the sentinel lymph node may be expressed by a second color which is different from the first color, using near-infrared fluorescence. The second color may be mainly expressed by one of red color, blue color and green color. Thus, FIG. 18A to FIG. 18C show that the living tissue and the sentinel lymph node can be clearly distinguished from each other. In an embodiment of the present invention, the second color is expressed by one of red color, blue color and green color, but it is not limited thereto and any color which can be distinguished from the first color is available.

Figure 19:
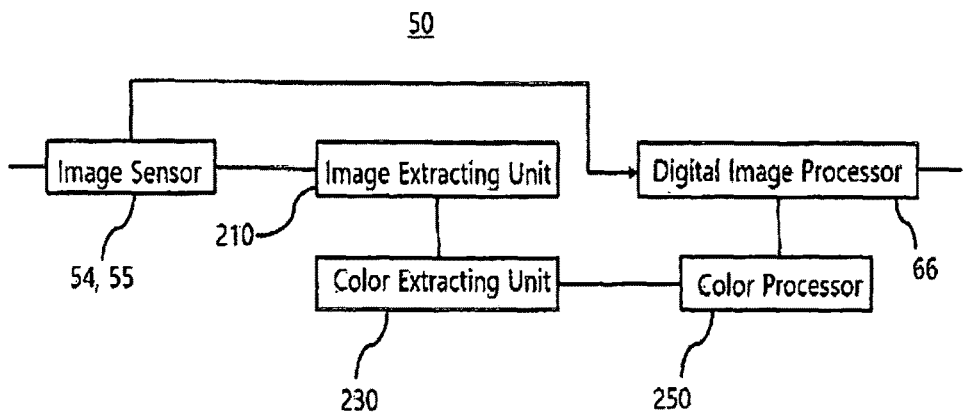
FIG. 19 is a schematic diagram of a multispectral image processor for implementing colors of a white reflection light image and a near-infrared fluorescence image according to an embodiment of the present invention.

FIG. 19 is a schematic diagram of a multispectral image processor for implementing colors of a white reflection light image and a near-infrared fluorescence image according to an embodiment of the present invention.

Referring to FIG. 19, a multispectral image processor 50 may comprise image sensors 54, 55, a digital image processor 66, an image extracting unit 210, a color extracting unit 230, a color processor 250.

The image sensors 54, 55 may perform image processing for images of a visible light region and a near-infrared region. The image extracting unit 210 may extract an image of the visible light region of images of the visible light region and the near-infrared region processed by the image sensors 54, 55 as a main image. In this case, the main image may be expressed by the first color.

The color extracting unit 230 may extract a color histogram by analyzing data of the first color for the main image extracted by the image extracting unit 210. At this time, the color extracting unit 230 may analyze a frequency distribution of data of the first color which is constituting the main image and may generate the color histogram that sequentially displays data of the first color having a high frequency according to the frequency distribution.

The color processing unit 250 may set a color having a little or no frequency in the color histogram extracted by the color extracting unit 230 and set the color to the second color which is different from the first color.

The digital image processor 66 may process the image of the visible light region to be implemented in the first color and the image of the near-infrared region to be implemented in the second color set by the color processing unit 250.

The digital image processor 66 may select the second color as the representative color and perform image processing for the image of the visible light region according to a state of an executed application. For example, the image extracting unit 210 may extract an image of the near-infrared region of images of the visible light region and the near-infrared region processed by the image sensors 54, 55 as a main image.

In this case, the main image, namely, the image of the near-infrared region may be expressed by the first color. The color extracting unit 230 may extract a color histogram by analyzing data of the first color for the image of the near-infrared region extracted by the image extracting unit 210.

The color processing unit 250 may set a color having a little or no frequency in the color histogram extracted by the color extracting unit 230 and set the color to the second color which is different from the first color.

The digital image processor 66 may process the image of the near-infrared region to be implemented in the first color and the image of the visible light region to be implemented in the second color set by the color processing unit 250.

Figure 20:
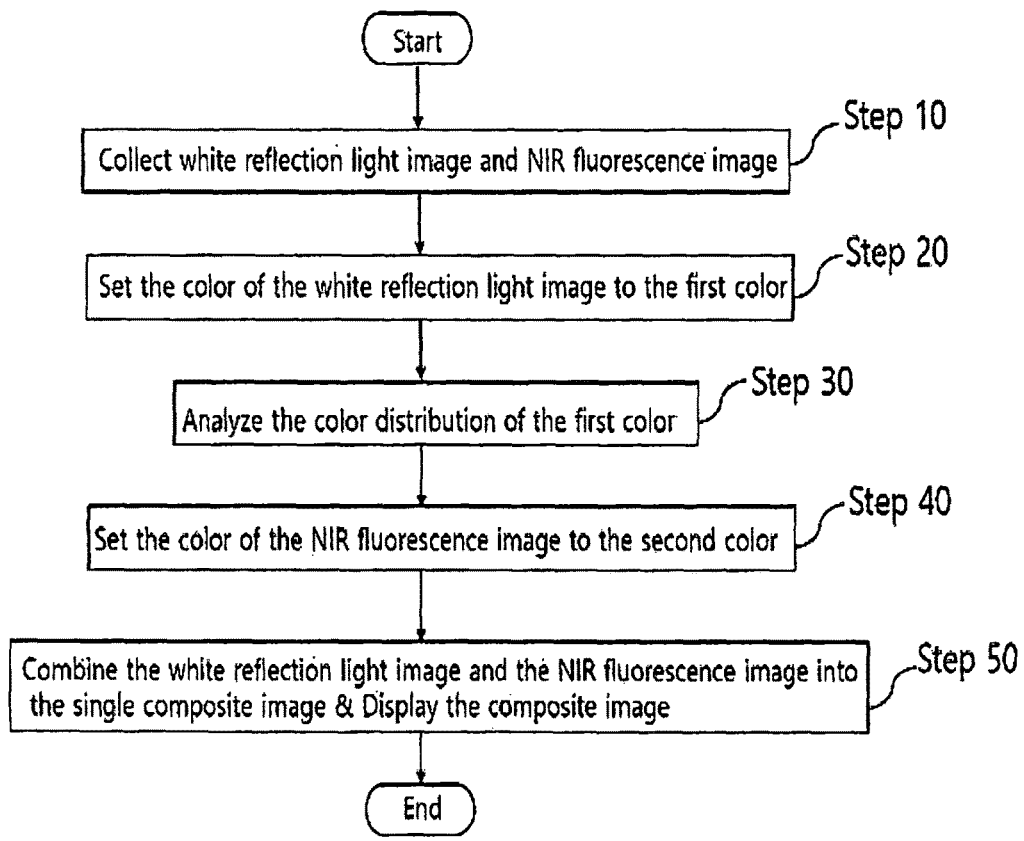
FIG. 20 is a block diagram sequentially illustrating a process of forming a composite image by superimposing a white reflection light image and a near-infrared fluorescence image according to an embodiment of the present invention.

FIG. 20 is a block diagram sequentially illustrating a process of forming a composite image by superimposing a white reflection light image and a near-infrared fluorescence image according to an embodiment of the present invention.

As shown in FIG. 20, first, a white reflection light image and a near-infrared fluorescence image are collected. (Step 10) Then, a color which is composed of a combination of red (R), green (G) and blue (B) is set to the first color for the collected white reflection light image. (Step 20) Then, a color distribution is analyzed through a color histogram for the first color. (Step 30) A color which is not expressed in the white reflection light image is set to the second color for the near-infrared fluorescence image, based on the analysis of the color distribution after analyzing the color distribution of the first color (Step 40). After that, the white reflection light image set to the first color and the near-infrared fluorescence image set to the second color are superimposed onto each other and generated as a single composite image, the single composite image is displayed. (Step 50)

That is, on generating the composite image, an image processing is performed so that the white reflection light image signal is implemented with a color composed of red (R), green (G), and blue (B) in a pixel in which a near-infrared fluorescence image signal is not detected, and is performed so that the near-infrared fluorescence image signal is implemented with a color which is not expressed in the white reflection light image in a pixel in which the near-infrared fluorescence image signal is detected.

Meanwhile, if a color of the living tissue includes all colors, a color of the sentinel lymph node to be implemented is at least same to the color of any part of the living tissue. In this case, it is substantially difficult to distinguish the living tissue and the sentinel lymph node as described with reference to FIG. 3.

In this regard, it is possible to distinguish the living tissue from the sentinel lymph node by the following method in another embodiment of the present invention.

Figure 21:
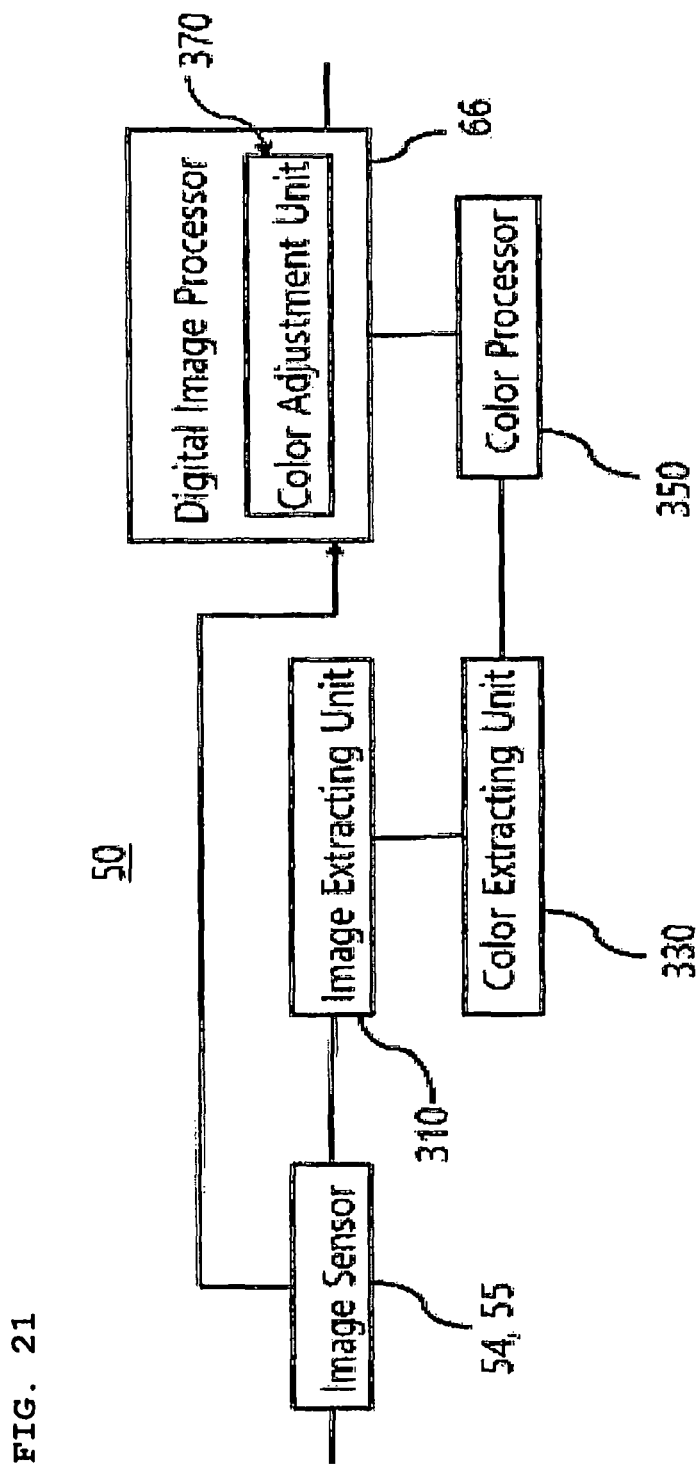
FIG. 21 is a schematic diagram of a multispectral image processor for implementing colors of a white reflection light image and a near-infrared fluorescence image according to an another embodiment of the present invention.

FIG. 21 is a schematic diagram of a multispectral image processor for implementing colors of a white reflection light image and a near-infrared fluorescence image according to an another embodiment of the present invention.

As shown in FIG. 21, a multispectral image processor 50 to calibrate a color may comprise image sensors 54, 55, a digital image processor 66, an image extracting unit 310, a color extracting unit 330 and a color processor 350.

The image sensors 54, 55 may perform image processing for images of a visible light region and a near-infrared region. The image extracting unit 310 may extract an image of the visible light region of images of the visible light region and the near-infrared region processed by the image sensors 54, 55 as a main image. In this case, the main image may be expressed by the first color.

The color extracting unit 330 may extract a color histogram by analyzing data of the first color for the main image extracted by the image extracting unit 310. At this time, the color extracting unit 330 may analyze a frequency distribution of data of the first color which is constituting the main image and may generate the color histogram that sequentially displays data of the first color having a high frequency according to the frequency distribution.

The color processing unit 350 may set a color having a little or no frequency in the color histogram extracted by the color extracting unit 330 and set the color to the second color which is different from the first color.

At this time, if there is a frequency of all the colors in the color histogram extracted by the color extracting unit 330, the color processing unit 350 may set an arbitrary color to the second color because it cannot set the second color which is different from the first color.

The arbitrary color may be any one of red color (R), green color (G), and blue color (B), but may be a color that can be more easily distinguished from the first color. That is, it is preferable to select a color having a small frequency in the color histogram.

The digital image processor 66 may include a color adjustment unit 370. Also the digital image processor 66 may process the image of the visible light region to be implemented in the first color and the image of the near-infrared region to be implemented in the second color set by the color processing unit 350.

The color adjusting unit 370 compares the first color, which is the image of the visible light region, with the second color, which is the image of the near-infrared region, and if the first color and the second color are the same, the color adjusting unit 30 may adjust at least one of a grayscale of the first color and a grayscale of the second color.

At this time, after setting a difference between the grayscale of the first color and the grayscale of the second color to be equal to or greater than a specific threshold value, the grayscale of the first color and the grayscale of the second color may be relatively adjusted so that the first color and the second color can be visually distinguished.

For example, as a first method, a grayscale value of the first color is fixed, a grayscale value of the second color may be adjusted so that the difference between the grayscale value of the first color and the grayscale value of the second color is above the threshold value. As a second method, a grayscale value of the second color is fixed, the grayscale value of the first color may be adjusted so that the difference between the grayscale value of the first color and the grayscale value of the second color is above the threshold value. As a third method, both of the grayscale value of the first color and the grayscale value of the second value may be adjusted so that the difference between the grayscale value of the first color and the grayscale value of the second color is equal to or greater than the threshold value.

The digital image processor 66 may select the second color as the representative color and perform image processing for the image of the visible light region according to a state of an executed application. For example, the image extracting unit 310 may extract an image of the near-infrared region of images of the visible light region and the near-infrared region processed by the image sensors 54, 55 as a main image.

In this case, the main image, namely, the image of the near-infrared region may be expressed by the first color. The color extracting unit 330 may extract a color histogram by analyzing data of the first color for the image of the near-infrared region extracted by the image extracting unit 310.

The color processing unit 350 may set a color having a little or no frequency in the color histogram extracted by the color extracting unit 330 and set the color to the second color which is different from the first color.

At this time, if there is a frequency of all the colors in the color histogram extracted by the color extracting unit 330, the color processing unit 350 may set an arbitrary color to the second color because it cannot set the second color which is different from the first color.

The arbitrary color may be any one of red color (R), green color (G), and blue color (B), but may be a color that can be more easily distinguished from the first color. That is, it is preferable to select a color having a small frequency in the color histogram.

The digital image processor 66 may include a color adjustment unit 370. Also the digital image processor 66 may process the image of the visible light region to be implemented in the first color and the image of the near-infrared region to be implemented in the second color set by the color processing unit 350

If the first color, which is the image of the visible light region is same with the second color, which is the image of the near-infrared region, the color adjustment unit 370 may adjust in a same way as described above. A description thereof will be omitted because it has already been explained.

Figure 22:
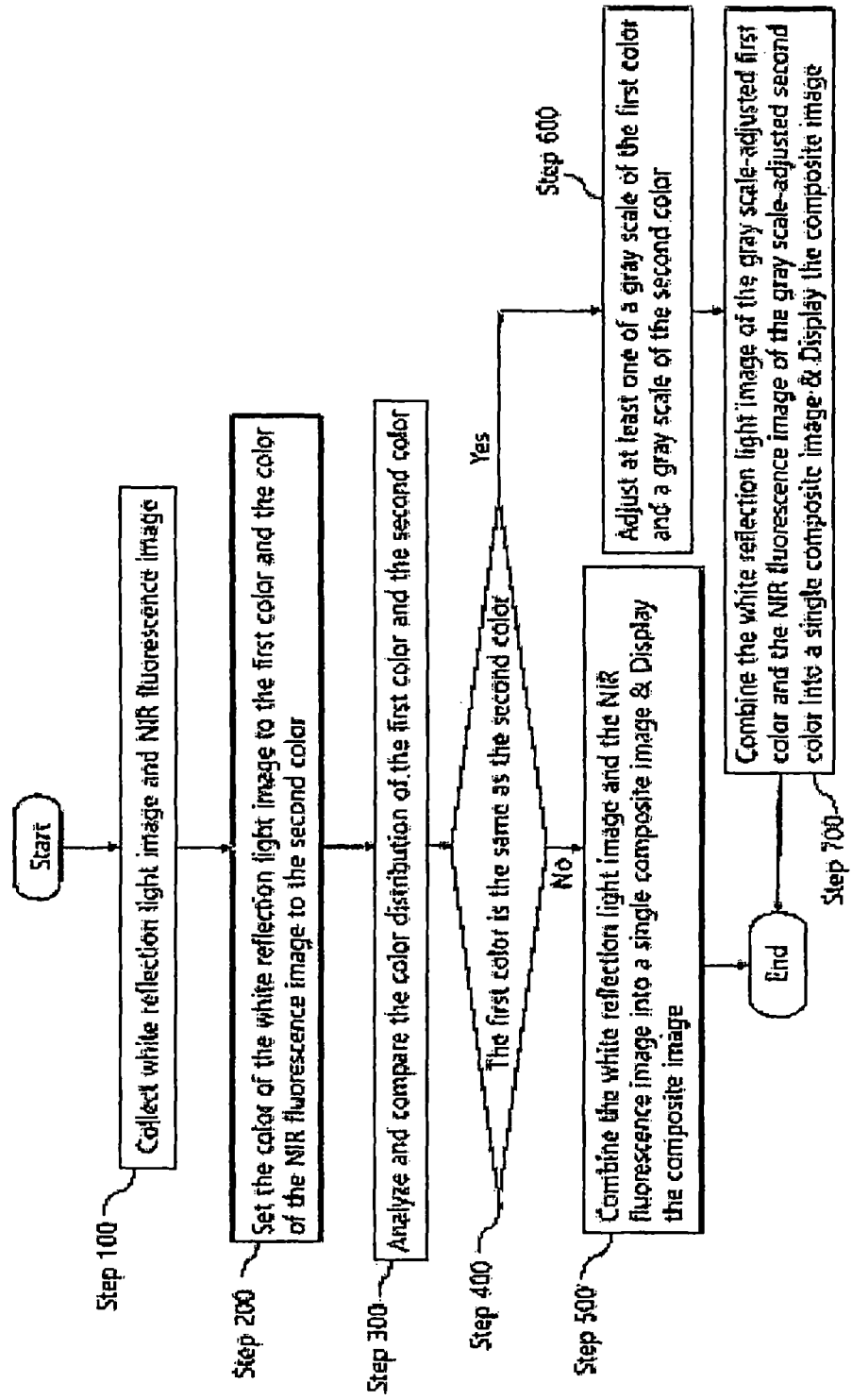
FIG. 22 is a block diagram sequentially illustrating a process of forming a composite image by superimposing a white reflection light image and a near-infrared fluorescence image according to an another embodiment of the present invention.

FIG. 22 is a block diagram sequentially illustrating a process of forming a composite image by superimposing a white reflection light image and a near-infrared fluorescence image according to an another embodiment of the present invention.

As shown in FIG. 22, first, a white reflection light image and a near-infrared fluorescence image are collected. (Step 100) Then, a color which is composed of a combination of red (R), green (G) and blue (B) is set to the first color for the collected white reflection light image and a color, which is at least one of red (R), green (G) and blue (B) is to the second color for the collected near-infrared fluorescence image. (Step 200) Then, a color distribution is analyzed and compared for the first color and the second color. (Step 300)

Then, it is determined whether the first color and the second color are the same based on a comparative analysis of the color distribution. (Step 400) If the first color and the second color are not same with each other, a white light image set to the first color and a near-infrared fluorescent image set to the second color are generated as a single composite image and then the composite image is displayed. (Step 500) If the first color and the second color are the same, at least one of the first color and the second color is adjusted. (Step 600) At this time, a grayscale of the two colors is relatively adjusted so that the first color and the second color can be distinguished from each other. Thereafter, the white light image of the first color and the near-infrared fluorescence image of the second color, which are grayscale-adjusted, are generated as single composite image and the composite image is displayed. (Step 700)

That is, on generating the composite image, an image processing is performed so that the white reflection light image signal is implemented with a color composed of red (R), green (G), and blue (B) in a pixel in which a near-infrared fluorescence image signal is not detected, and is performed so that the near-infrared fluorescence image signal is implemented with at least one of red (R), green (G), and blue (B) in a pixel in which the near-infrared fluorescence image signal is detected. At this time, if the color of the white reflection light image and the color of the near-infrared fluorescence image are the same, the image processing is performed so that at least one of the grayscales of the two colors is adjusted.

Figure 23:
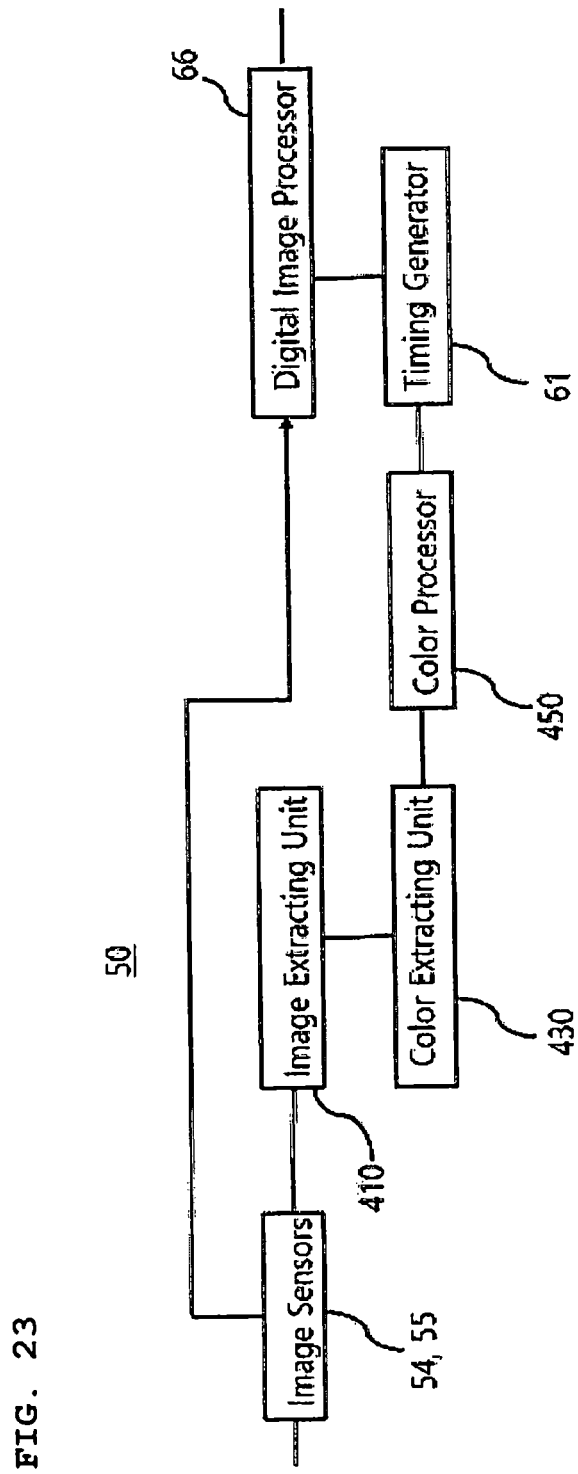
FIG. 23 is a schematic diagram of a multispectral image processor for implementing colors of a white reflection light image and a near-infrared fluorescence image according to a further another embodiment of the present invention.

FIG. 23 is a schematic diagram of a multispectral image processing unit for implementing colors of a white reflection light image and a near-infrared fluorescence image according to a further another embodiment of the present invention.

Referring to FIG. 23, A multispectral image processing unit 50 to calibrate a color may comprise image sensors 54, 55, a digital image processor 66, an image extracting unit 410, a color extracting unit 430, a color processor 450 and a timing generator 61.

The function of each component included in the multispectral image processing unit 50 is the same as that of components shown in FIG. 19, and a description thereof will be omitted.

If the first color, which is the image of the visible light region, and the second color, which is the image of the near infrared region, are same with each other, the timing generator 61 controls the timing pulse of the near-infrared fluorescence image signal so that the implemented second color is discontinuously expressed.

For example, the timing pulse of the near-infrared fluorescence image signal for displaying the near-infrared fluorescence is adjusted periodically or non-periodically with a time interval. Accordingly, the first color representing the living tissue is continuously displayed and the second color representing the sentinel lymph node in the living node is displayed by blinking in an image displayed on the display unit 80.

The multispectral image processing unit 50 according to an embodiment of the present invention may adjust the grayscale of the first color and the grayscale of the second color in a first manner or adjust the timing pulse of the near-infrared fluorescence image signal so that the second color is discontinuously implemented in a second manner if the first color is same with the second color. That is, the multispectral image processing unit 50 may individually perform image processing in the first manner and the second manner or perform image processing by combining the first manner and the second manner.

The invention has been described in detail with reference to exemplary embodiments thereof. However, it will be appreciated by those skilled in the art that changes may be made in these embodiments without departing from the principles and spirit of the invention, the scope of which is defined in the appended claims and their equivalents.

What is claimed is:

1. A device for detecting near-infrared (NIR) fluorescence at a sentinel lymph node (SLN), the device comprising:
   a white light source configured to irradiate white light onto an object;
   a near-infrared (NIR) excitation light source configured to irradiate near-infrared (NIR) excitation light onto the object;
   an optical analyzing assembly configured to transmit white reflection light reflected off the object when the white light is irradiated on the object and near-infrared (NIR) fluorescence reflected off the object when the near-infrared (NIR) excitation light is irradiated on the object;
   a multispectral image processing unit configured to detect the white reflection light and the near-infrared (NIR) fluorescence, transmitted from the optical analyzing assembly, and process the white reflection light and the near-infrared (NIR) fluorescence as a visible (VIS) reflection light image signal and a near-infrared (NIR) fluorescence image signal, respectively; and
   a display unit configured to output a composite image obtained by combining the visible (VIS) reflection light image signal and the near-infrared (NIR) fluorescence image signal, processed by the multispectral image processing unit,
   wherein the multispectral image processing unit performs image processing so that the visible (VIS) reflection light image signal is expressed by a first color composed of red (R), green (G) and blue (B) in a pixel from which an NIR where the near-infrared (NIR) fluorescence image signal is not detected, and the NIR near-infrared (NIR) fluorescent image signal is expressed by a second color, which is different from the first color, in a pixel where the near-infrared (NIR) fluorescent image signal is detected.

2. The device of claim 1, wherein the multispectral image processing unit extracts a color histogram for the visible reflection light image signal and sets a color having a little or no frequency in the color histogram to the second color.

3. A device for detecting near-infrared (NIR) fluorescence at a sentinel lymph node (SLN), the device comprising:
   a white light source configured to irradiate white light onto an object;
   a near-infrared (NIR) excitation light source configured to irradiate near-infrared (NIR) excitation light onto the object;
   an optical analyzing assembly configured to transmit white reflection light reflected off the object when the white light is irradiated on the object and near-infrared (NIR) fluorescence reflected off the object when the near-infrared (NIR) excitation light is irradiated on the object;
   a multispectral image processing unit configured to detect the white reflection light and the near-infrared (NIR) fluorescence, transmitted from the optical analyzing assembly, and process the white reflection light and the near-infrared (NIR) fluorescence as a visible (VIS) reflection light image signal and a near-infrared (NIR) fluorescence image signal, respectively; and
   a display unit configured to output a composite image obtained by combining the visible (VIS) reflection light image signal and the near-infrared (NIR) fluorescence image signal, processed by the multispectral image processing unit,
   wherein the multispectral image processing unit performs image processing so that the visible (VIS) reflection light image signal is expressed by a first color composed of red (R), green (G) and blue (B) in a pixel from which an NIR where the near-infrared (NIR) fluorescence image signal is not detected, and the NIR near-infrared (NIR) fluorescent image signal is expressed by a second color, which is at least one of red (R), green (G) and blue (B), in a pixel where the near-infrared (NIR) fluorescent image signal is detected,
   wherein if the second color is same with the first color, the multispectral image processing unit controls a grayscale of at least one of the first color and the second color to be adjusted or controls a timing pulse of the near-infrared (NIR) fluorescent image signal so that the second color is discontinuously implemented.

4. The device of claim 3, wherein the multispectral image processing unit extracts a color histogram for the visible reflection light image signal and sets a color having a little or no frequency in the color histogram to the second color.

5. The device of claim 3, wherein the grayscale of the first color and the grayscale of the second color are adjusted so that a difference between the grayscale of the first color and the grayscale of the second color is equal to or greater than a specific threshold value.

6. The device of claim 3, wherein the grayscale of the first color and the grayscale of the second color is relatively adjusted.

7. The device of claim 3, wherein the timing pulse of the near-infrared fluorescence image signal is adjusted periodically or non-periodically with a time interval.

8. A method for detecting near-infrared (NIR) fluorescence at a sentinel lymph node (SLN), the method comprising:
   irradiating white light and NIR near-infrared (NIR) excitation light onto an object;
   collecting white reflection light reflected off the object when the white light is irradiated onto the object and near-infrared (NIR) fluorescence reflected off the object when the near-infrared (NIR) excitation light is irradiated onto the object;
   performing image processing so that the white reflection light is expressed by a first color which is composed of red (R), green (G), blue (B) and the near-infrared (NIR) fluorescence is expressed by a second color which is different from the first color; and
   generating a composite image by combining the white reflection light having the first color and the near-infrared (NIR) fluorescence having the second color.

9. A method for detecting near-infrared (NIR) fluorescence at a sentinel lymph node (SLN), the method comprising:
   irradiating white light and NIR near-infrared (NIR) excitation light onto an object;
   collecting white reflection light reflected off the object when the white light is irradiated onto the object and near-infrared (NIR) fluorescence reflected off the object when the near-infrared (NIR) excitation light is irradiated onto the object;
   performing image processing so that the white reflection light is expressed by a first color which is composed of red (R), green (G), blue (B) and the near-infrared (NIR) fluorescence is expressed by a second color; and
   generating a composite image by combining the white reflection light having the first color and the near-infrared (NIR) fluorescence having the second color,
   wherein if the second color is same with the first color, an image processing is performed so that a grayscale of at least one of the first color and the second color is adjusted or a timing pulse of a near-infrared (NIR) fluorescence image signal is adjusted so that the second color is discontinuously implemented.

10. The method of claim 9, wherein the grayscale of the first color and the grayscale of the second color are adjusted so that a difference between the grayscale of the first color and the grayscale of the second color is equal to or greater than a specific threshold value.

11. The method of claim 9, wherein the grayscale of the first color and the grayscale of the second color is relatively adjusted.

* * * * *